United States Patent
Raslambekov

(10) Patent No.: US 11,801,122 B1
(45) Date of Patent: Oct. 31, 2023

(54) SYSTEM AND A METHOD FOR DETERMINING A TOOTH T-MARKING

(71) Applicant: Oxilio Ltd, Larnaca (CY)

(72) Inventor: Islam Khasanovich Raslambekov, Long Island City, NY (US)

(73) Assignee: Oxilio Ltd, Larnaca (CY)

( * ) Notice: Subject to any disclaimer, the term of this patent is extended or adjusted under 35 U.S.C. 154(b) by 0 days.

(21) Appl. No.: 18/116,485

(22) Filed: Mar. 2, 2023

(51) Int. Cl.
G06T 19/20 (2011.01)
A61C 7/00 (2006.01)
G06T 1/00 (2006.01)
A61C 9/00 (2006.01)

(52) U.S. Cl.
CPC .............. *A61C 7/002* (2013.01); *A61C 9/004* (2013.01); *G06T 1/00* (2013.01); *G06T 2207/30036* (2013.01)

(58) Field of Classification Search
CPC ........... G06T 2207/30036; G06T 19/20; G06T 7/0012; G06T 2200/04; G06T 19/00; G06T 17/00; G06T 17/205; A61C 7/002; A61C 9/004
See application file for complete search history.

(56) References Cited

U.S. PATENT DOCUMENTS

| | | | |
|---|---|---|---|
| 8,118,593 B2 | 2/2012 | Imgrund et al. | |
| 9,345,558 B2 | 5/2016 | Oda et al. | |
| 9,492,247 B2 | 11/2016 | Ruiz-Vela et al. | |
| 9,622,834 B2 | 4/2017 | Chapoulaud et al. | |
| 9,782,236 B2 | 10/2017 | Sporbert et al. | |
| 10,166,088 B2 | 1/2019 | Sachdeva et al. | |
| 10,610,332 B2 | 4/2020 | Wu et al. | |
| 10,856,954 B1 | 12/2020 | Raslambekov | |
| 10,993,782 B1 | 5/2021 | Raslambekov | |
| 11,007,035 B2 | 5/2021 | Fares et al. | |
| 11,065,085 B2 | 7/2021 | Martz et al. | |
| 11,166,787 B1 | 11/2021 | Raslambekov | |
| 11,259,897 B1 | 3/2022 | Raslambekov | |
| 2019/0043255 A1* | 2/2019 | Somasundaram | G06T 17/20 |
| 2020/0297457 A1 | 9/2020 | Shah et al. | |
| 2021/0200188 A1 | 7/2021 | Shah et al. | |
| 2021/0259808 A1 | 8/2021 | Ben-Gal Nguyen et al. | |

* cited by examiner

*Primary Examiner* — Hau H Nguyen
(74) *Attorney, Agent, or Firm* — BCF LLP

(57) ABSTRACT

A method and electronic device for determining a T-marking of a given tooth of a subject are provided. The method comprises: obtaining a 3D digital model representative of a surface of a plurality of subject's teeth including the given tooth; obtaining a reference plane extending along an occlusal surface of the given tooth; generating groupings of the mesh elements along a surface of the given tooth; identifying normals at vertices defining each grouping, and projecting the normals onto the reference plane; determining a labiolingual line of the T-marking as a line of best fit of ends of the projected normals with starts in plane origin; determining, a mesiodistal line of the T-marking as a line extending in the reference plane through the reference plane origin and perpendicular to the labiolingual line; and determining the T-marking of the given tooth as the labiolingual line intersecting the mesiodistal line.

20 Claims, 17 Drawing Sheets

SYSTEM AND A METHOD FOR DETERMINING A TOOTH T-MARKING

FIELD

The present technology relates broadly to determining an orthodontic treatment for a subject; and more specifically, to methods and systems for determining a T-marking for a given tooth of the subject.

BACKGROUND

A typical orthodontic treatment comprises a number of consecutive treatment steps in which orthodontic appliances are consecutively used to apply forces to a subject's teeth to move the subject's teeth from a respective start position to a desired position.

Simulation of the movement of the subject's teeth may be used for planning one or more of the orthodontic treatment steps, including determining and modelling application of the forces causing the teeth to perform the movements towards to the desired position.

Generally speaking, for more accurate and effective simulation of the movements of the subject's teeth, determination of certain orthodontic landmarks of a given tooth of the subject may be required. Such landmarks include a mesial point and a distal point of an occlusal surface of the given tooth. Various applications of these landmarks with respect to the simulation of the movements of the given tooth include one or more of: segmenting the given tooth from neighboring teeth and an adjacent gingiva; determining a tooth axis and a center of resistance of the given tooth; determining an application point for a given force causing the given tooth to move to the desired position; determining an attachment point for an orthodontic attachment for the given tooth; determining an amount of tooth material of the given tooth to be removed in case of a determined future collision; amongst others.

Also, using the mesial and distal points allows determining another orthodontic landmark, a T-marking, which is identified as an intersection of a mesiodistal line, extending through the mesial and distal points, and a labiolingual line, perpendicular to the mesiodistal line. For example, the T-marking can be used for determining an orientation of the given tooth relative to other teeth while modelling the movements of the subject's teeth in the course of the orthodontic treatment. In another example, the T-marking can be used for analyzing differences in sizes and mutual positions between upper and lower teeth of the subject, which is also known as a Bolton analysis.

Typically, the mesial and distal points or the entire T-marking are determined manually, by a dental practitioner, such as an orthodontist. However, as the placement of the T-marking depends largely on the expertise and experience of the particular practitioner, this approach may be inaccurate, which may further affect accuracy of one of the above applications of the so determined mesial and distal points. Also, this approach may not provide desired consistency in determining the points, and can thus cause variation in positioning of these points from tooth to tooth or subject to subject. As a result, effectiveness of the orthodontic treatment can be lowered.

Certain prior art approaches have been proposed to address the above-identified problem of manual determination of the T-markings.

United States Patent Application Publication No.: 2021/0200,188-A1, published on Jul. 1, 2021, assigned to Ormco Corp, and entitled "SYSTEMS AND METHODS FOR DESIGNING AND MANUFACTURING AN ORTHODONTIC APPLIANCE", discloses systems and methods of defining a trimline in relation to modeled teeth including a three-dimensional model of one or more intraoral surfaces of the patient. The trimline is for use to manufacture an aligner. For one or more pairs of adjacent teeth, a scallop plane is defined based on a scallop factor. The scallop plane is used to determine the position of scallop points on a line around each tooth adjacent to an interproximal region of the pair of teeth. Transition points are then defined on the line around each tooth apically of the scallop points, and the points connected to form an initial connector curve. The initial connector curve is projected on to a mesh of the three-dimensional model, and smoothing applied to the resulting segmented connector curve. The smoothed connector curves are then joined by teeth curves to form the trimline.

U.S. Pat. No. 11,166,787-B1, issued on Nov. 9, 2021, assigned to Arkimos Ltd, and entitled "ORTHODONTIC ATTACHMENT SYSTEMS AND METHODS", discloses method for determining a coupling point for an attachment on a tooth of a subject comprising: obtaining a digital 3D representation of the tooth to which the attachment will be coupled; obtaining attachment data indicative of the attachment to be coupled to the tooth; determining, on the digital 3D representation of the tooth, a plurality of excluded areas for the coupling point based on the digital 3D representation of the tooth and the attachment data; determining the coupling point by identifying an area on the tooth which is not in the plurality of excluded areas; and storing, in a memory of the computer system, the determined coupling point.

U.S. Pat. No. 10,856,954-B1, issued on Dec. 8, 2020, assigned to Arkimos Ltd, and entitled "SYSTEMS AND METHODS FOR DETERMINING TOOTH CENTER OF RESISTANCE", discloses a method and a system for determining a center of resistance point of a tooth for orthodontic treatment planning. The method comprises: obtaining a tooth mesh from image data associated with a tooth crown of a patient; identifying a mesiodistal center of the tooth crown; determining a reference plane in the image data to extend through the mesiodistal center; determining an intersection curve based on an intersection of the reference plane and the tooth mesh, the intersection curve following a shape of the surface of the crown at the reference plane; determining a tooth axis of the tooth crown based on the intersection curve; determining a crown height of the tooth crown based on the tooth axis; and determining the center of resistance of the tooth based on the determined crown height and the determined tooth axis.

It is desired to provide improved methods and systems for determining the orthodontic landmarks.

SUMMARY

Developers of the present technology have devised methods and systems for determining the T-marking associated with a given tooth based on analyzing a surface topography of the given tooth. More specifically, certain non-limiting embodiments of the present technology are based on a premise that determining the positions of the mesial and distal points for each of the subject's teeth can be more accurate and thus effective if they are derived from the T-marking that has been determined as dividing convex portions of the surface topography of the given tooth.

Further, the mesial and distal points can be determined at intersections of the so determined T-marking with the occlusal surface of the given tooth.

Thus, such a method, which is automated and therefore not reliant on practitioner experience, may allow for improved consistency in determining the T-marking, which may further allow for more predictable results of the applications of the mesial and distal points for the given tooth and other teeth of the subject's, such as determining the tooth axis or determining the application point for the given force to be exerted onto the given tooth during the treatment. As a result, the so determined orthodontic landmarks can allow for a more accurate modelling of the tooth movements of the subject's teeth, which can further translate to more effective orthodontic treatments.

More specifically, in accordance with a first broad aspect of the present technology, there is provided a method for determining a T-marking of a given tooth of a subject. The T-marking includes a labiolingual line and a mesiodistal line. The method is executable by a processor. The method comprises: obtaining, by the processor, a 3D digital model representative of a surface of a plurality of subject's teeth including the given tooth, the 3D digital model comprising a mesh comprising mesh elements interconnecting a plurality of vertices; obtaining, by the processor, a reference plane which extends along an occlusal surface of the given tooth; generating, by the processor, groupings of the mesh elements, each grouping comprising a sub-group of the mesh elements connecting a respective sub-group of vertices of the plurality of vertices in a tree-like configuration, the groupings being based on one or more apices of the surface of the given tooth; identifying, by the processor, normal vectors at vertices defining each grouping, and projecting the normal vectors onto the reference plane; determining the labiolingual line as a line, extending in the reference plane, which is a line of best fit of ends of the projected unitized normal vectors with starts in plane origin; determining, by the processor, the mesiodistal line as a line extending in the reference plane through the reference plane origin and perpendicular to the labiolingual line; determining, by the processor, the T-marking of the given tooth as the labiolingual line intersecting the mesiodistal line; and storing, by the processor, data indicative of the T-marking associated with the given tooth for further use in determining an orthodontic treatment for the subject.

In some implementations of the method, the method further comprises after the projecting the normal vectors onto the reference plane, moving an origin of each of the normal vectors to a reference vertex on an occlusal surface of the given tooth, and wherein the determining the line of best fit comprises determining the line of best fit with respect to the origins.

In some implementations of the method, the generating a given grouping comprises: obtaining, by the processor, data of a tooth axis associated with the given tooth; and identifying, by the processor, edges of the mesh that are most aligned with the tooth axis associated with the given tooth when traversing the plurality of vertices representative of the given tooth.

In some implementations of the method, the identifying the edges most aligned with the direction of the tooth axis comprises: identifying, by the processor, a given vertex associated with the given tooth; identifying, by the processor, a set of neighboring vertices of the given vertex, each one of the set of neighboring vertex being connected to the given vertex through a respective edge; projecting, by the processor, each one of the set of neighboring vertices on the tooth axis of the given tooth; and determining, by the processor, a given most aligned edge from the given vertex as the respective edge that connects the given vertex with that one of the set of neighboring vertices, a projection of which on the tooth axis is outermost on the tooth axis.

In some implementations of the method, the generating the groupings comprises generating the groupings from vertices within a predetermined distance from a reference point on an occlusal surface of the given tooth.

In some implementations of the method, the method further comprises determining if at least one vertex of a given grouping is located more than a predetermined distance, along the surface of the given tooth, from a reference point on an occlusal surface of the given tooth; and in response to determining that the at least one vertex of the given grouping is located more than the predetermined distance from the reference vertex, removing the at least one vertex of the given grouping from further consideration.

In some implementations of the method, the method further comprises omitting a given grouping from further consideration if it has less than a predetermined number of vertices.

In some implementations of the method, the method further comprises fitting a sphere to a given grouping by minimizing a sum of distances from the vertices of the grouping to a surface of the sphere, and omitting a given grouping from further consideration if one or more of the following apply: (i) the fit sphere does not intersect a tooth axis of the given tooth; (ii) the fit sphere has a radius of more than a predetermined threshold radius; and (iii) a center of the fit sphere is more than a predetermined distance from the tooth axis of the given tooth.

In some implementations of the method, the fitting the sphere is performed if the given tooth is identified as a molar, premolar or a canine tooth.

In some implementations of the method, the method further comprises determining an identity of the given tooth, the determining comprising: identifying, by the processor, in the 3D digital model, occlusal vertices representative of the occlusal surface of the given tooth; separating the occlusal vertices using the reference plane; determining, by the processor, that the given tooth is a molar or premolar tooth if more than a predetermined portion of the occlusal vertices lie between the reference plane and a surface of a gingiva around the given tooth; and determining, by the processor, that the given tooth is a incisor or canine tooth if less than the predetermined portion of the occlusal vertices lie between the reference plane and the surface of the gingiva of the given tooth.

In some implementations of the method, the method further comprises reducing a complexity of the mesh of the 3D digital model, before generating the groupings, by removing mesh elements whilst retaining the vertices.

In some implementations of the method, the method further comprises, for each grouping, randomly removing one or more vertices.

In some implementations of the method, the method further comprises obtaining data of a tooth axis associated with the given tooth, and wherein the obtaining the reference plane comprises obtaining the reference plane such that the reference plane extends through the tooth axis associated with the given tooth.

In some implementations of the method, the obtaining the data of the tooth axis comprises determining, by the processor, the tooth axis of the given tooth, the determining the tooth axis comprising: identifying a reference vertex on an occlusal surface of the given tooth; identifying occlusal vertices of the plurality of vertices which are within a predetermined distance from the reference vertex; determining a normal vector for each of the occlusal vertices; determining an average normal vector for the occlusal vertices, and determining the tooth axis of the given tooth as extending in a direction of the determined average normal vector through the reference vertex.

In some implementations of the method, the reference vertex is selected at a geometrical center of the occlusal surface.

In some implementations of the method, the determining the mesiodistal line comprises building a bounding box around the groupings; and using the bounding box to truncate the mesiodistal line to dimensions of the given tooth.

In accordance with a second broad aspect of the present technology, there is provided an electronic device for determining a T-marking of a given tooth of a subject. The T-marking includes a labiolingual line and a mesiodistal line. The electronic device comprises a processor and a non-transitory computer-readable medium storing instructions. The processor, upon executing the instructions, is configured to: obtain a 3D digital model representative of a surface of a plurality of subject's teeth including the given tooth, the 3D digital model comprising a mesh comprising mesh elements interconnecting a plurality of vertices; obtain a reference plane which extends along an occlusal surface of the given tooth; generate groupings of the mesh elements, each grouping comprising a sub-group of the mesh elements connecting a respective sub-group of vertices of the plurality of vertices in a tree-like configuration, the groupings being based on one or more apices of the surface of the given tooth; identify normal vectors at vertices defining each grouping, and projecting the normal vectors onto the reference plane; determine the labiolingual line as a line, extending in the reference plane, which is a line of best fit of ends of the projected unitized normal vectors with starts in plane origin; determine the mesiodistal line as a line extending in the reference plane through the reference plane origin and perpendicular to the labiolingual line; determine the T-marking of the given tooth as the labiolingual line intersecting the mesiodistal line; and store data indicative of the T-marking associated with the given tooth for further use in determining an orthodontic treatment for the subject.

In some implementations of the electronic device, after projecting the normal vectors onto the reference plane, the processor is further configured to move an origin of each of the normal vectors to a reference vertex on an occlusal surface of the given tooth, and determine the line of best fit with respect to the origins.

In some implementations of the electronic device, to generate a given grouping, the processor is configured to identify edges of the mesh that are most aligned with the tooth axis associated with the given tooth when traversing the plurality of vertices representative of the given tooth along the tooth axis thereof.

In some implementations of the electronic device, to identify the edges most aligned with the direction of the tooth axis, the processor is configured to: identify a given vertex of the plurality of vertices associated with the given tooth; identify a set of neighboring vertices of the given vertex, each one of the set of neighboring vertex being connected to the given vertex through a respective edge; project each one of the set of neighboring vertices on the tooth axis of the given tooth; and determine a given most aligned edge from the given vertex as the respective edge that connects the given vertex with that one of the set of neighboring vertices, a projection of which on the tooth axis is topmost in a direction of the traversing the plurality of vertices.

In the context of the present specification, unless expressly provided otherwise, the term "orthodontic treatment" is broadly referred to as any type of medical intervention aimed at correcting malocclusions associated with the teeth of the subject or moving the subject's teeth for any reason, including surgical and non-surgical manipulations, such as, but not limited to, using one or more of aligners, brackets, multi-strand wires, strips, retainers, and plates. Further, the orthodontic treatment, as referred to herein, may be determined automatically by a software, based on image data and other inputs associated with the subject, or semi-automatically with input from a practitioner in the field of dentistry (such as an orthodontist, a maxillofacial surgeon, for example).

In the context of the present specification, unless expressly provided otherwise, a computer system may refer, but is not limited to, an "electronic device", an "operation system", a "system", a "computer-based system", a "controller unit", a "control device" and/or any combination thereof appropriate to the relevant task at hand.

In the context of the present specification, unless expressly provided otherwise, the expression "computer-readable medium" and "memory" are intended to include media of any nature and kind whatsoever, non-limiting examples of which include RAM, ROM, disks (CD-ROMs, DVDs, floppy disks, hard disk drives, etc.), USB keys, flash memory cards, solid-state-drives, and tape drives.

In the context of the present specification, a "database" is any structured collection of data, irrespective of its particular structure, the database management software, or the computer hardware on which the data is stored, implemented or otherwise rendered available for use. A database may reside on the same hardware as the process that stores or makes use of the information stored in the database or it may reside on separate hardware, such as a dedicated server or plurality of servers.

In the context of the present specification, unless expressly provided otherwise, the words "first", "second", "third", etc. have been used as adjectives only for the purpose of allowing for distinction between the nouns that they modify from one another, and not for the purpose of describing any particular relationship between those nouns.

Embodiments of the present technology each have at least one of the above-mentioned object and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of embodiments of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description which is to be used in conjunction with the accompanying drawings, where.

DETAILED DESCRIPTION

Certain aspects and embodiments of the present technology are directed to methods and systems for determining T-markings for subject's teeth, which can further be used, for example, in determining an orthodontic treatment for the subject.

More specifically, the present methods and systems are directed to automatically determining the T-markings based on the surface topography of the subject's teeth. Thus, methods and systems provided herein, according to certain non-limiting embodiments of the present technology, allow one or more of: achieving a higher accuracy in planning and predictability of orthodontic treatments, improving overall safety and comfort to the subject during an orthodontic treatment, and resolving malocclusions more efficiently and effectively.

Certain aspects and embodiments of the present technology will now be described below with reference to example orthodontic treatments.

Orthodontic Treatment

Orthodontic treatments are used for treating different conditions relating to teeth misalignment or malocclusion, including but not limited to one or more of: tooth rotation, tooth intrusion/extrusion, tooth translation, and interdental space management. Interdental space management may include one or more of closing embrasures, creating interproximal contacts, opening embrasures, and eliminating interproximal contacts.

An orthodontic appliance 10 used in orthodontic treatments, according to certain non-limiting embodiments of the present technology, include a bracket/archwire system 10a (FIGS. 1 and 2), or an aligner system 10b (FIGS. 3 and 4), amongst others.

Figure 1:
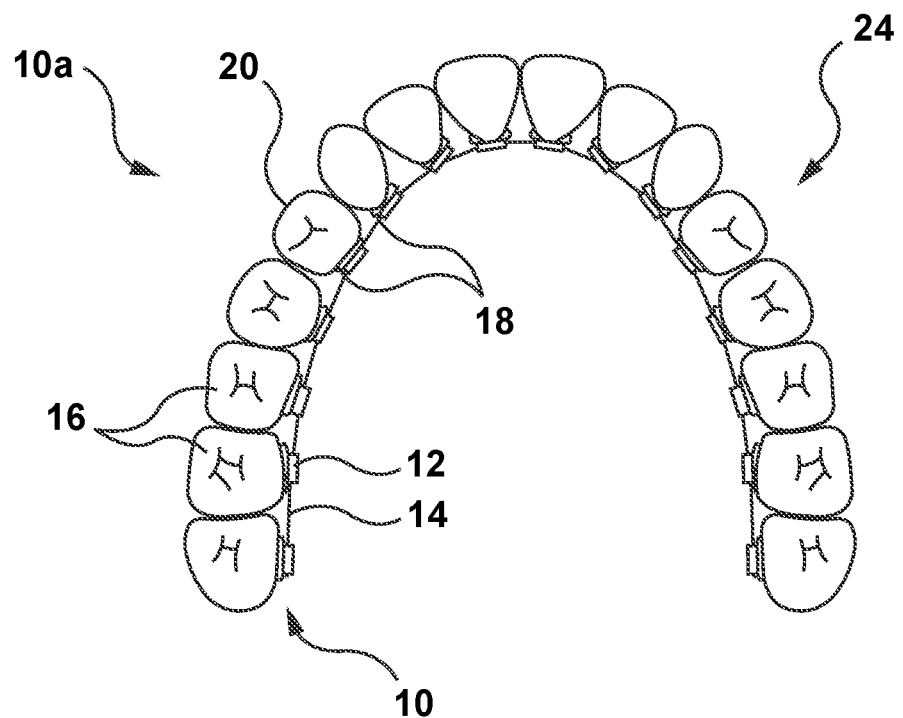
FIG. 1 depicts a schematic diagram of a subject's teeth to which a given orthodontic appliance used for treating orthodontic disorders is attached, in accordance with certain non-limiting embodiments of the present technology.
Figure 2:
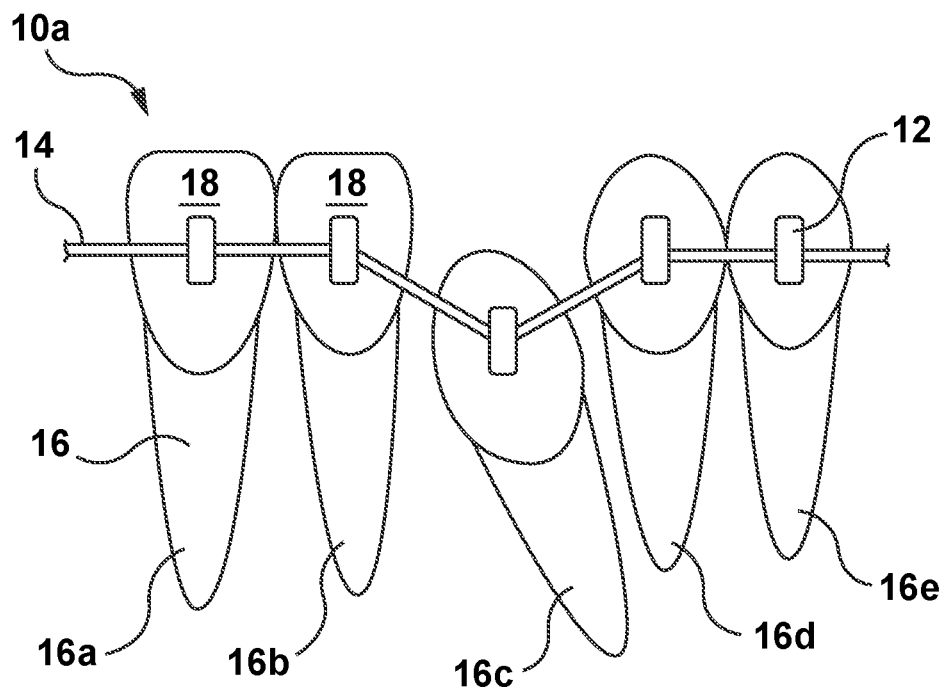
FIG. 2 depicts a schematic diagram of the given orthodontic appliance attached to five teeth of the subject's teeth of FIG. 1, in accordance with certain non-limiting embodiments of the present technology.

In the bracket/archwire system 10a of FIGS. 1 and 2, according to certain non-limiting embodiments of the present technology, there are provided brackets 12 and an archwire 14. The bracket/archwire system 10a is depicted as applied to upper teeth 16 of an upper arch form 24 of a subject (not shown), with the brackets 12 being attached to internal surfaces 18 of the upper teeth 16 in a lingual configuration. However, it is contemplated that the orthodontic appliance 10 may be applied in other configurations, such as in a buccal configuration (attached to external surfaces 20 of the upper teeth 16, for example. It is also contemplated that in other non-limiting embodiments of the present technology of the present technology, the orthodontic appliance 10 may be applied on upper teeth 16 of an upper arch form 24 of the subject in any one of a palatal configuration (attached to inner-sides of teeth of the upper jaw) and a labial configuration (attached to outer-sides of the teeth of the upper jaw) (not shown).

The brackets 12 are provided on respective ones of the upper teeth 16 (shown individually as 16a, 16b, 16c, 16d, 16e in FIG. 2), and the archwire 14 extends between, and is connected to, each of the brackets 12. In the illustrated example, the subject has a malocclusion—that is, a misalignment—of the tooth 16c for which the orthodontic treatment includes an upward movement of the tooth 16c so that the tooth 16c is aligned with neighboring the upper teeth 16a, 16b, 16d, 16e. The archwire 14 is made of a shape memory alloy, such as Nitinol™ and is shaped such that it exerts an upward force to the tooth 16c in use. The archwire 14 can also be made of any other shape memory alloy, or of a material with elastic properties. In certain non-limiting embodiments of the present technology, the bracket/archwire system 10a is designed to impart the orthodontic treatment determined using certain non-limiting embodiments of the present technology of the methods and systems, which will be described below.

Figure 3:
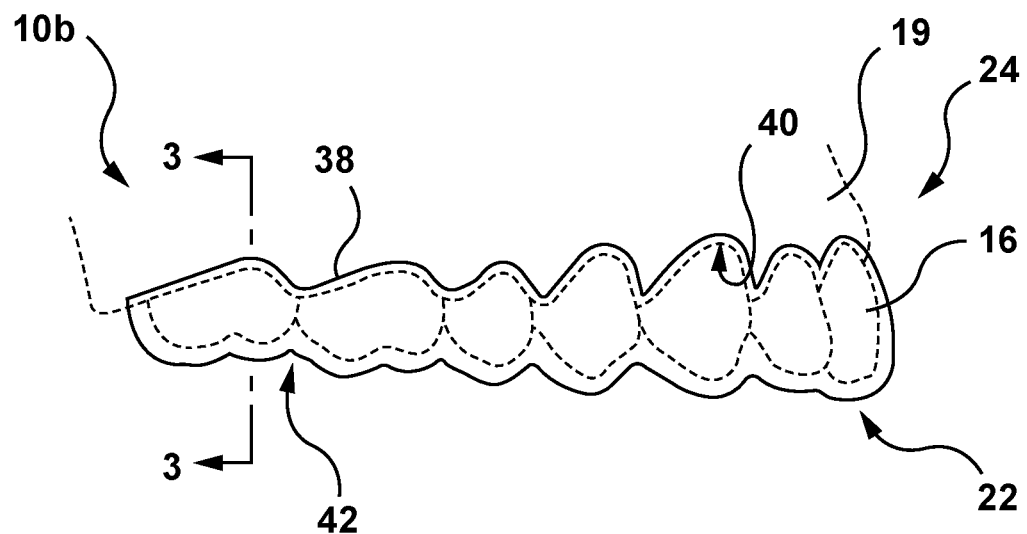
FIGS. 3 and 4 depict side and cross-sectional views, respectively, of another orthodontic appliance which is configured for receiving at least some of the subject's teeth of FIG. 1 for treating the orthodontic disorders, in accordance with certain non-limiting embodiments of the present technology.
Figure 4:
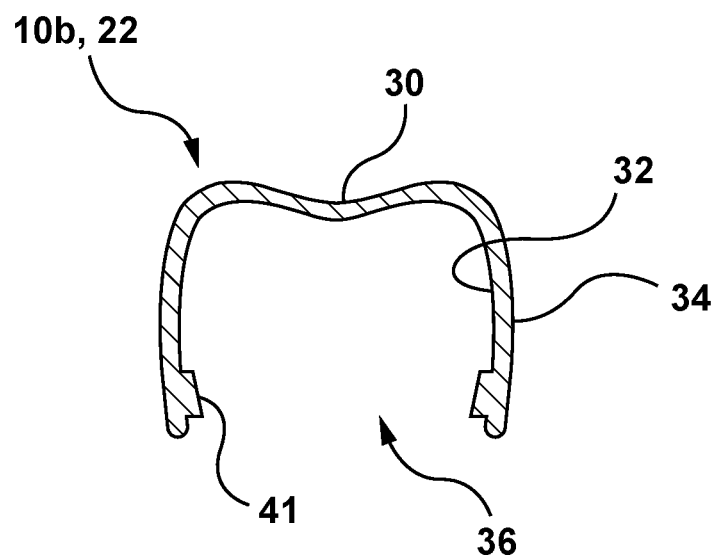

In the aligner system 10b of FIGS. 3 and 4, there is provided an aligner 22 made according to certain aspects and non-limiting embodiments of the present technology, and arranged to impart the orthodontic treatment determined or optimized by methods and systems of the present technology.

As illustrated in FIG. 3, the aligner 22 is for the upper arch form 24 (also referred to as "upper arch" or "upper dental arch") of another subject. However, in other non-limiting embodiments of the present technology (not shown), the aligner 22 is provided for a lower arch form of the subject. In yet other non-limiting embodiments of the present technology, different configurations of the aligner 22 for both the lower arch form and the upper arch form 24 can be provided.

The aligner 22 comprises an aligner body 30 having an inner surface 32 and an outer surface 34. The inner surface 32 defines a channel 36 for receiving at least some upper teeth 16 of the upper arch of the subject. At least one edge 38 of the channel 36 is shaped for intimately following an upper gingiva 19 along a gumline 40 of the subject. In the embodiment of FIGS. 3 and 4, the aligner 22 is arranged to receive all the upper teeth 16 of the upper arch form 24 of the subject. In certain other non-limiting embodiments of the present technology, the aligner 22 is arranged to receive some, not all, of the upper teeth 16.

According to certain non-limiting embodiments of the present technology, a thickness of the aligner body 30, measurable from the inner surface 32 to the outer surface 34 along a direction substantially normal vector to the inner surface 32, is substantially uniform across the aligner body 30.

In other non-limiting embodiments of the present technology, the thickness of the aligner body 30 is variable. For example, in some embodiments, the aligner 22 may further include retentive features for retaining the aligner 22 with respect to the upper teeth 16. Such retentive features can be for example aligner blocks, such as a given block 41, extending outwardly from the inner surface 32 to engage the upper teeth 16 in use. Other retentive features can be aligner recesses defined in the inner surface 32 and sized to engagingly receive blocks affixed to the upper teeth 16 (not shown).

The aligner 22 is made of a polymer, such as a thermoplastic material. In certain non-limiting embodiments of the present technology, the aligner 22 is made of polyvinyl chloride (PVC). In certain other non-limiting embodiments of the present technology, the aligner 22 is made of polyethylene terephthalate glycol (PETG). Other suitable materials can also be used to form the aligner 22. In the case of PETG and PVC, the aligner 22 is substantially transparent. The aligner 22 may be made of other materials having properties that are typically desirable in aligner 22, such as one or more of: low surface roughness, high translucency and mechanical strength adapted for bearing typical orthodontic loads.

It will be appreciated that the present technology can be applied to design and/or make different types, shapes, sizes and configurations of the orthodontic appliance 10, such as, without limitation, multi-strand wires, strips, retainers, and plates. It will also be appreciated that the orthodontic appliance 10 may be used for treating any type of teeth misalignment or malocclusion.

Orthodontic treatments using the orthodontic appliance 10, such as the bracket/archwire system 10a of FIGS. 1 and 2, or the aligner system 10b of FIGS. 3 and 4, comprise sequential treatment steps, in certain non-limiting embodiments of the present technology, in which the orthodontic appliance 10 are applied to the upper teeth 16 at each treatment step to apply forces. The orthodontic appliance 10 and/or applied forces may be the same or different in each treatment step.

Figure 5:
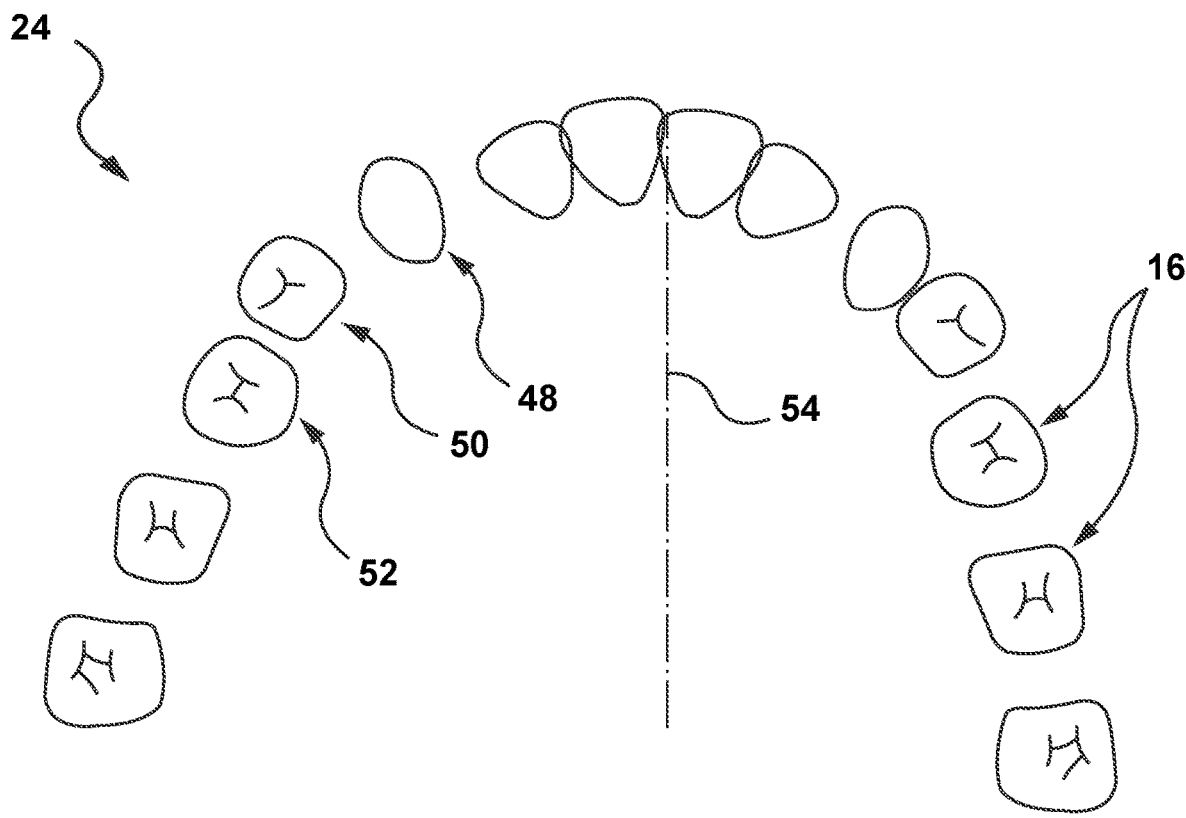
FIGS. 5 and 6 depict a general top view and a magnified top view, respectively, of the subject's teeth in current and desired positions thereof, in accordance with certain non-limiting embodiments of the present technology.
Figure 6:
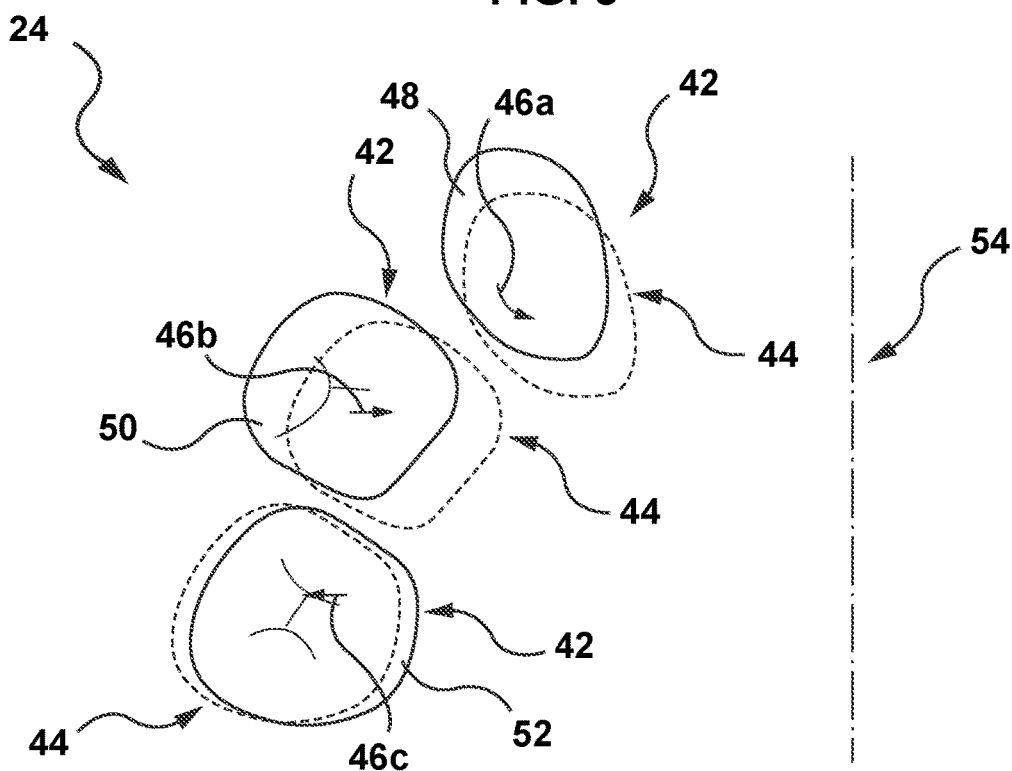

Referring now to FIGS. 5 and 6, generally, in determining the orthodontic treatment, an initial position 42 of the given one of the upper teeth 16 is determined, such as by imaging of the upper teeth 16, using an intraoral scanner, for example, or by taking a physical mold. A desired position 44 of the upper teeth 16, which can be, for example, associated with alignment of the given one of the upper teeth 16 therewithin, can then be identified. This can be performed manually, semi-automatically, or automatically. In certain non-limiting embodiments of the present technology, the desired position 44 is determined by the orthodontic practitioner. Depending on the initial and desired positions 42, 44 of the upper teeth 16, a trajectory 46 of the movement of the given one of the upper teeth 16 from the initial position 42 to the desired position 44 is determined. In certain non-limiting embodiments of the present technology, the trajectory is one or more of a direct linear path, a plurality of stepped linear paths, and a rotational path.

FIG. 5 depicts a representation of the initial positions 42 of the upper teeth 16 of the subject in the upper arch form 24, and FIG. 6 shows an enlarged view of three of the upper teeth 16 of FIG. 5: an upper right lateral tooth 48, an upper right cuspid tooth 50 and an upper right first bicuspid tooth 52. The initial positions 42 of these three teeth 48, 50, 52 are shown in solid line. The desired positions 44 of each of these three teeth 48, 50, 52 are shown in dotted line. As can be seen, to be positioned in the desired position 44, the upper right lateral tooth 48 will need to be moved laterally and rotationally along a trajectory 46a, the upper right cuspid tooth 50 will need to be moved linearly towards a middle 54 of the jaw along the trajectory 46b, and the upper right first bicuspid 52 will need to be moved linearly away from the middle 54 of the jaw along the trajectory 46c.

As stated above, the orthodontic treatment may comprise a number of treatment steps for moving the given one of the upper teeth 16 from the initial position 42 to the desired position 44. Each treatment step may be defined by a different load provided by different configurations of at least one of the above-mentioned implementations of the orthodontic appliance 10. It may be determined, for example, that the given one of the upper teeth 16 is to be moved 3 mm in three consecutive treatment steps in order to minimize any damage to the upper gingiva 19 and tooth roots.

Certain methods of determination of orthodontic treatment steps in orthodontic treatments are described in a co-owned U.S. Pat. No. 10,993,782-B1 issued on May 4, 2021, and entitled "SYSTEMS AND METHODS FOR DETERMINING A TOOTH TRAJECTORY", the content of which is incorporated herein by reference in its entirety. Also, in some non-limiting embodiments of the present technology, the steps for the orthodontic treatment can be determined in accordance with methods disclosed in a co-owned U.S. Pat. No. 11,259,897-B1 issued on Mar. 1, 2022, and entitled "SYSTEMS AND METHODS FOR DETERMINING AN ORTHODONTIC TREATMENT", the content of which is incorporated herein by reference in its entirety.

Figure 7:
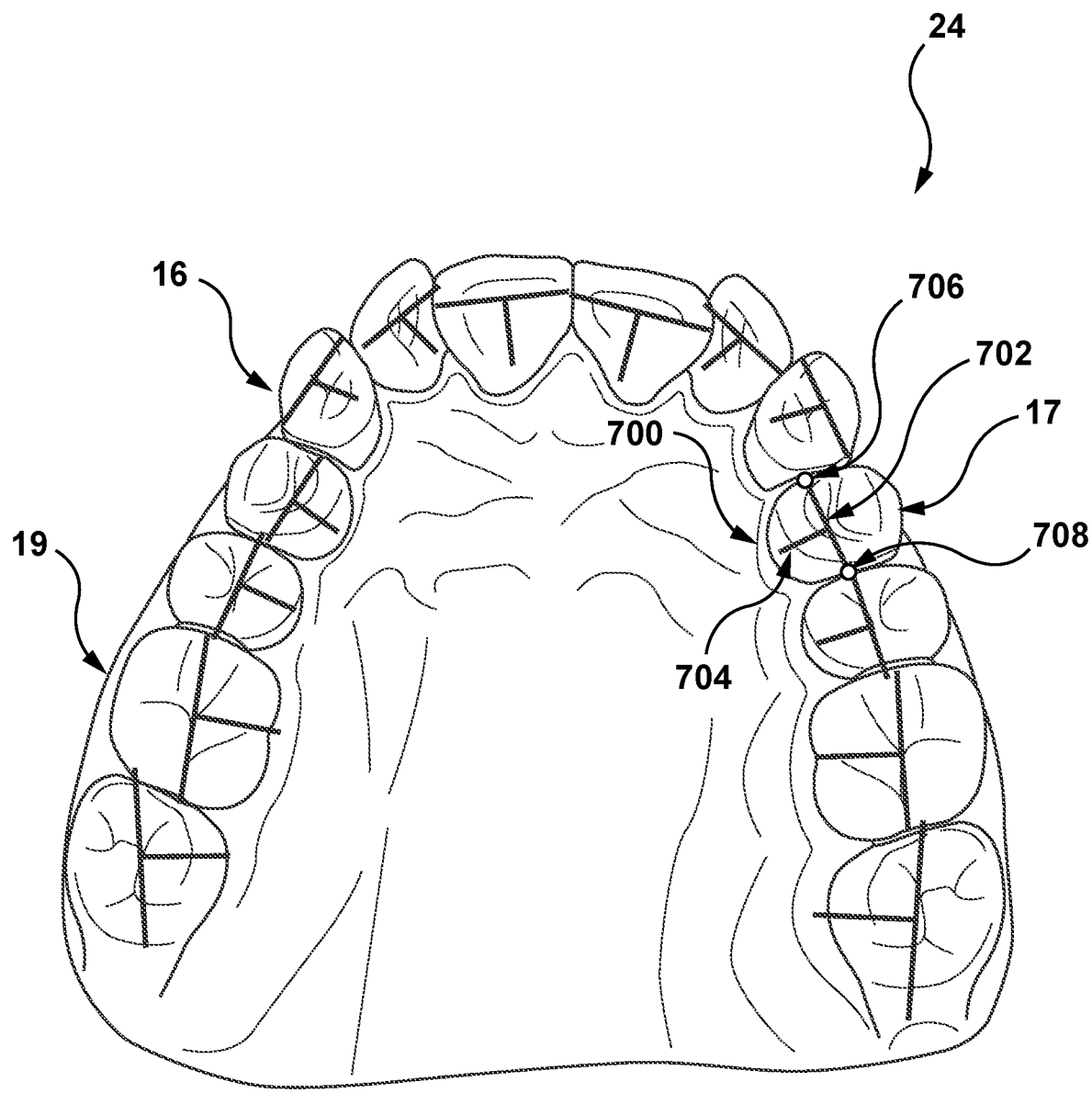
FIG. 7 depicts a bottom elevation view of the subject's teeth of FIG. 1 with T-markings applied thereto, in accordance with certain non-limiting embodiments of the present technology.

However, for a more accurate modelling of the movements of the upper teeth 16 from the initial to desired positions 42, 44 in the course of the planned orthodontic treatment, certain orthodontic landmarks may need to be determined. Embodiments of the present technology are directed to determining T-markings for the subject's teeth, such as a T-marking 700 associated with a given tooth 17 as indicated on a bottom elevation view of the upper arch form 24 depicted in FIG. 7, in accordance with certain non-limiting embodiments of the present technology.

Broadly speaking, the T-marking 700 of the given tooth 17 comprises (i) a mesiodistal line 702 extending along an occlusal surface of the given tooth 17 and indicative of a width of a crown of the given tooth 17; and (ii) a labiolingual line 704 extending perpendicular to the mesiodistal line 702. In some non-limiting embodiments of the present technology, the labiolingual line 704 originates from a midpoint of the mesiodistal line 702. According to certain non-limiting embodiments of the present technology, the T-marking 700 can enable determining the orientation of the given tooth 17 relative to other ones of the upper teeth 16 in each given position thereof, which may further enable determining an amount of movement required, such as rotation and/or translation as mentioned above, for the given tooth 17 to arrive at the desired position 44. In another example, the T-marking applied to each one of the upper teeth 16 and lower teeth (not depicted) of the subject can be used for analyzing relative positions therebetween, which is also known as a Bolton analysis.

Also, the T-marking 700 may enable determining additional orthodontic landmarks, such as a mesial point 706 and a distal point 708 determined on the occlusal surface of the given tooth 17 as points of intersection of the T-marking 700 with side surfaces of the given tooth 17. The mesial and distal points 706, 708 can also be used in modelling the movements of the given tooth 17 for the orthodontic treatment planning. More specifically, the mesial and distal points 706, 708, determined in accordance with certain non-limiting embodiments of the present technology, can be used for one or more of: (i) determining a center of resistance associated with the given tooth 17 further enabling determining a given force to be applied to the given tooth 17 causing the given tooth 17 towards the desired position 44; (ii) segmenting the given tooth 17 in 3D digital models (such as a 3D digital model 1102 depicted in FIG. 11) from neighboring teeth and the upper gingiva 19; (iii) determining configurations and application points for orthodontic appliances and components thereof, such as, without limitation, those of the brackets 12 of the bracket/archwire system 10a, the given block 41 of the aligner 22, attachments (not depicted) used in concert with the aligner 22, pontics (not depicted) used to close gaps between the teeth; (iv) generate augmented representations (such as 3D digital models) of the given tooth 17 and surrounding tissues thereof, such as the upper gingiva 19; and (v) determining an amount of tooth material of the given tooth 17 to be removed to avoid a potential collision with the neighboring teeth; and others.

Typically, the T-marking 700 or at least one of the mesial and distal points 706, 708 defining the T-marking 700 are determined manually, by the orthodontic partitioner, such as an orthodontist, involved in determining the orthodontic treatment for the subject. However, the actual placement of the T-marking 700 by the orthodontic practitioner is very subjective and can depend on their experience amongst other factors. Therefore, such manually placed T-markings, and hence mesial and distal points, may be determined inconsistently for different teeth of the same subject, as well as between different subjects. This may further result in an inaccurate determination of the movements of the subject's teeth, thereby affecting the effectiveness of the so planned orthodontic treatment.

Thus, developers of the present technology have devised methods and systems for determining the T-marking 700 associated with the given tooth 17 less subjectively: based on surface topography features thereof. More specifically, certain non-limiting embodiments of the present technology are directed to methods and systems for determining the T-marking 700 as dividing certain convex portions (such as cusps) of the surface topography of the given tooth 17. This may allow determining the respective T-marking consistently for each one of the subject's teeth, such as the upper teeth 16, and thus increasing accuracy of the implementation of the orthodontic treatment according to the determined plan thereof.

How the T-marking 700 can be determined, in accordance with certain non-limiting embodiments of the present technology, will be described below with reference to FIGS. 10 to 21.

System

Figure 8:
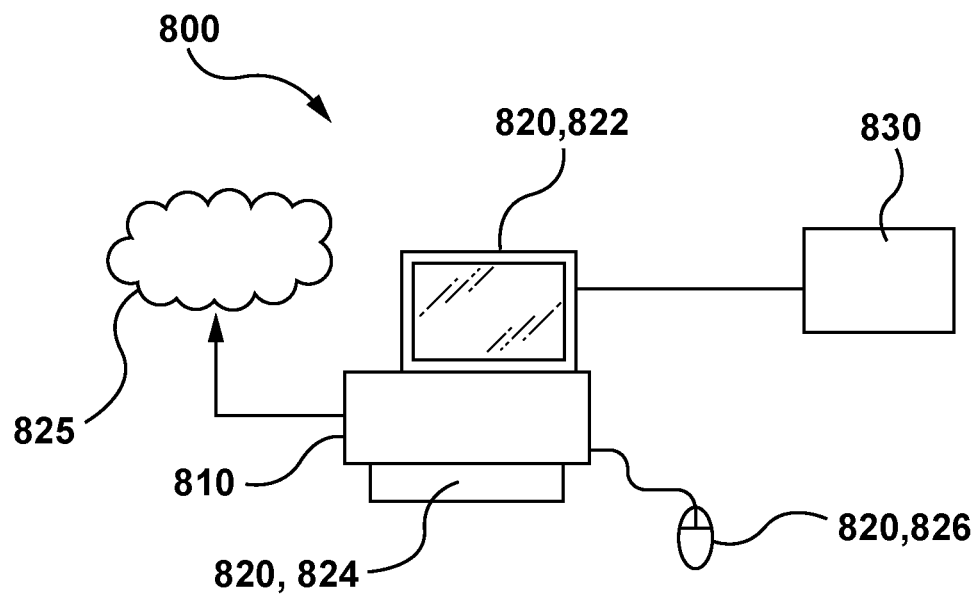
FIG. 8 depicts a schematic diagram of a system for determining a T-marking for a given tooth of the subject's teeth of FIG. 2, in accordance with certain embodiments of the present technology.
Figure 9:
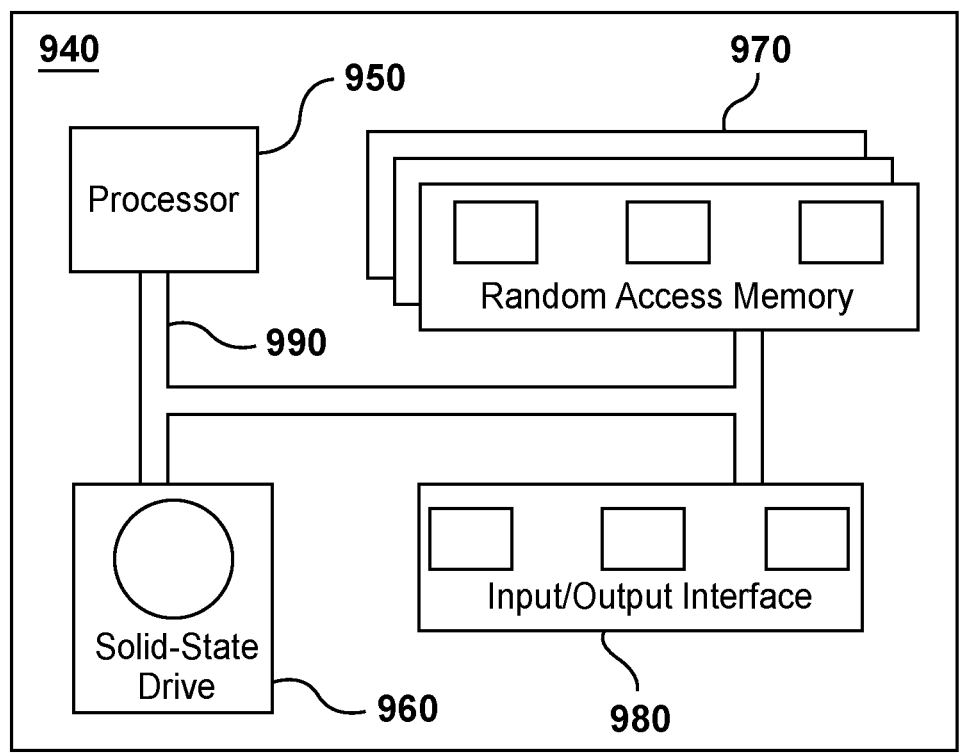
FIG. 9 depicts a schematic diagram of a computing environment of the system of FIG. 8, in accordance with certain embodiments of the present technology.

With reference to FIGS. 8 and 9, there is depicted a schematic diagram of a system 400 suitable for determining the respective T-marking for the subject's teeth, such as the T-marking 700 of the given tooth 17, in accordance with certain non-limiting embodiments of the present technology.

It is to be expressly understood that the system 800 as depicted is merely an illustrative implementation of the present technology. Thus, the description thereof that follows is intended to be only a description of illustrative examples of the present technology. This description is not intended to define the scope or set forth the bounds of the present technology. In some cases, what is believed to be helpful examples of modifications to the system 800 may also be set forth below. This is done merely as an aid to understanding, and, again, not to define the scope or set forth the bounds of the present technology. These modifications are not an exhaustive list, and, as a person skilled in the art would understand, other modifications are likely possible. Further, where this has not been done (i.e., where no examples of modifications have been set forth), it should not be interpreted that no modifications are possible and/or that what is described is the sole manner of implementing that element of the present technology. As a person skilled in the art would understand, this is likely not the case. In addition, it is to be understood that the system 800 may provide in certain instances simple implementations of the present technology, and that where such is the case they have been presented in this manner as an aid to understanding. As persons skilled in the art would further understand, various implementations of the present technology may be of a greater complexity.

In certain non-limiting embodiments of the present technology, the system 800 of FIG. 8 comprises a computer system 810. The computer system 810 may be configured, by pre-stored program instructions, to determine and output, based on image data associated with the subject's teeth, the respective T-marking for the subject's teeth, such as the T-marking 700 for the given tooth 17. In some non-limiting embodiments of the present technology, the computer system 810 may further be configured to determine the orthodontic treatment for the subject, as will be described further. It should be noted that in various non-limiting embodiments of the present technology, the computer system 810 may be configured to execute the methods separately and/or independently. Further, the order of these steps may be changed without departing from the scope of the present technology.

To that end, in some non-limiting embodiments of the present technology, the computer system 810 is configured to receive the image data pertaining to the subject or to a given stage of the orthodontic treatment. For example, the computer system 810 may be configured to process the received image data to generate an arch form 3D digital model of the upper arch form 24. According to some non-limiting embodiments of the present technology, the computer system 810 may receive the image data via local input/output interface (such as USB, as an example, not separately depicted). In other non-limiting embodiments of the present technology, the computer system 810 may be configured to receive the image data over a communication network 825, to which the computer system 810 is communicatively coupled.

In some non-limiting embodiments of the present technology, the communication network 825 is the Internet and/or an Intranet. Multiple embodiments of the communication network may be envisioned and will become apparent to the person skilled in the art of the present technology. Further, how a communication link between the computer system 810 and the communication network 825 is implemented will depend, inter alia, on how the computer system 810 is implemented, and may include, but is not limited to, a wire-based communication link and a wireless communication link (such as a Wi-Fi communication network link, a 3G/4G communication network link, and the like).

It should be noted that the computer system 810 can be configured for receiving the image data from a vast range of devices. Some of such devices can be used for capturing and/or processing data pertaining to maxillofacial and/or cranial anatomy of the subject. In certain non-limiting embodiments of the present technology, the image data received from such devices is indicative of properties of anatomical structures of the subject, including: teeth, intraoral mucosa, maxilla, mandible, temporomandibular joint, and nerve pathways, among other structures. In some non-limiting embodiments of the present technology, at least some of the image data is indicative of properties of external portions of the anatomical structures, for example dimensions of a gingival sulcus, and dimensions of an external portion of the given tooth 17 (e.g., a crown of the given tooth 17) extending outwardly of the gingival sulcus. In some embodiments, the image data is indicative of properties of internal portions of the anatomical structures, for example volumetric properties of bone surrounding an internal portion of the given tooth 17 (e.g., a root of the given tooth 17) extending inwardly of the gingival sulcus. Under certain circumstances, such volumetric properties may be indicative of periodontal anomalies which may be factored into an orthodontic treatment plan. In some non-limiting embodiments of the present technology, the image data includes cephalometric image datasets. In some embodiments, the image data includes datasets generally intended for the practice of endodontics. In some embodiments, the image data includes datasets generally intended for the practice of periodontics.

In alternative non-limiting embodiments of the present technology, the computer system 810 may be configured to receive the image data associated with the subject directly from an imaging device 830 communicatively coupled thereto. Broadly speaking the imaging device 830 may be configured (for example, by a processor 950 depicted in FIG. 9) to capture and/or process the image data of the upper teeth 16 and the periodontium of the subject. In certain non-limiting embodiments of the present technology, the image data may include, for example, one or more of: (1) images of external surfaces of respective crown portions of the upper teeth 16, (2) images of an external surface of the periodontium including those of the upper gingiva 19, the alveolar maxillary bone, and images of superficial blood vessels and nerve pathways associated with the upper teeth 16; and (3) images of an oral region. By doing so, the imaging device 830 may be configured, for example, to capture the image data of the upper arch form 24 including the upper teeth 16 of the subject. It should be noted that although the examples provided herein are directed to receiving and processing the image data of the upper arch form 24 of the subject, it is done solely for the purposes of clarity of explanation of certain non-limiting embodiments of the present technology; therefore, the imaging device 830 may also be configured to capture and/or process image data of the lower arch form (not depicted) of the subject without departing from the scope of the present technology. It should also be noted that the image data may include two-dimensional (2D) data and/or three-dimensional data (3D). Further, in certain non-limiting embodiments of the present technology, the image data includes 2D data, from which 3D data may be derived, and vice versa.

In some non-limiting embodiments of the present technology, the imaging device 830 may comprise an intra-oral scanner enabling to capture direct optical impressions of the upper arch form 24 of the subject.

In a specific non-limiting example, the intraoral scanner can be of one of the types available from MEDIT, CORP. of 23 Goryeodae-ro 22-gil, Seongbuk-gu, Seoul, South Korea. It should be expressly understood that the intraoral scanner can be implemented in any other suitable equipment.

In other non-limiting embodiments of the present technology, the imaging device 830 may comprise a desktop scanner enabling to digitize a mold representing the upper arch form 24. In this regard, the mold may have been obtained via dental impression using a material (such as a polymer, e.g. polyvinyl-siloxane) having been imprinted with the shape of the intraoral anatomy it has been applied to. In the dental impression, a flowable mixture (i.e., dental stone powder mixed with a liquid in certain proportions) may be flowed such that it may, once dried and hardened, form the replica.

In a specific non-limiting example, the desktop scanner can be of one of the types available from DENTAL WINGS, INC. of 2251, ave Letourneux, Montreal (QC), Canada, H1V 2N9. It should be expressly understood that the desktop scanner can be implemented in any other suitable equipment.

Further, it is contemplated that the computer system 810 may be configured for processing of the received image data. The resulting image data of the upper arch form 24 received by the computer system 810 is typically structured as a binary file or an ASCII file, may be discretized in various ways (e.g., point clouds, polygonal meshes, pixels, voxels, implicitly defined geometric shapes), and may be formatted in a vast range of file formats (e.g., STL, OBJ, PLY, DICOM, and various software-specific, proprietary formats). Any image data file format is included within the scope of the present technology. For implementing functions described above, the computer system 810 may further comprise a corresponding computing environment.

With reference to FIG. 9, there is depicted a schematic diagram of a computing environment 940 suitable for use with some implementations of the present technology. The computing environment 940 comprises various hardware components including one or more single or multi-core processors collectively represented by the processor 950, a solid-state drive 960, a random-access memory 970 and an input/output interface 980. Communication between the various components of the computing environment 940 may be enabled by one or more internal and/or external buses 990 (e.g. a Peripheral Component Interconnect (PCI) bus, universal serial bus (USB), an IEEE 1394 "Firewire" bus, a Small Computer System Interface (SCSI) bus, a Serial-ATA (SATA) bus, an Aeronautical Radio INC (ARINC) bus, etc.), to which the various hardware components are coupled.

The input/output interface 980 allows enabling networking capabilities such as wire or wireless access. As an example, the input/output interface 980 comprises a networking interface such as, but not limited to, a network port, a network socket, a network interface controller and the like. Multiple examples of how the networking interface may be implemented will become apparent to the person skilled in the art of the present technology. For example, but without being limiting, the input/output interface 980 may implement specific physical layer and data link layer standard such as Ethernet™, Fibre Channel, Wi-Fi™ or Token Ring. The specific physical layer and the data link layer may provide a base for a full network protocol stack, allowing communication among small groups of computers on the same local area network (LAN) and large-scale network communications through routable protocols, such as Internet Protocol (IP).

According to implementations of the present technology, the solid-state drive 960 stores program instructions suitable for being loaded into the random-access memory 970 and executed by the processor 950, according to certain aspects and embodiments of the present technology. For example, the program instructions may be part of a library or an application.

In some non-limiting embodiments of the present technology, the computing environment 940 is implemented in a generic computer system which is a conventional computer (i.e. an "off the shelf" generic computer system). The generic computer system may be a desktop computer/personal computer, but may also be any other type of electronic device such as, but not limited to, a laptop, a mobile device, a smart phone, a tablet device, or a server.

As persons skilled in the art of the present technology may appreciate, multiple variations as to how the computing environment 940 can be implemented may be envisioned without departing from the scope of the present technology.

Referring back to FIG. 8, the computer system 810 has at least one interface device 820 for providing an input or an output to a user of the system 800, the at least one interface device 820 being in communication with the input/output interface 980. In the embodiment of FIG. 8, the interface device is a screen 822. In other non-limiting embodiments of the present technology, the at least one interface device 820 may be a monitor, a speaker, a printer or any other device for providing an output in any form such as an image form, a written form, a printed form, a verbal form, a 3D model form, or the like.

In the depicted embodiments of FIG. 8, the at least one interface device 820 also comprises a keyboard 824 and a mouse 826 for receiving input from the user of the system 800. Other interface devices 820 for providing an input to the computer system 810 can include, without limitation, a USB port, a microphone, a camera or the like.

The computer system 810 may be connected to other users, such as through their respective clinics, through a server (not depicted). The computer system 810 may also be connected to stock management or client software which could be updated with stock when the orthodontic treatment has been determined and/or schedule appointments or follow-ups with clients, for example.

According to the non-limiting embodiments of the present technology, the processor 950 may be configured to determine the T-markings for the subject's teeth, such as the upper teeth 16, and use them for determining the orthodontic treatment. How these non-limiting embodiments can be implemented will be described with reference to FIGS. 10 to 21.

Methods

Figure 10:
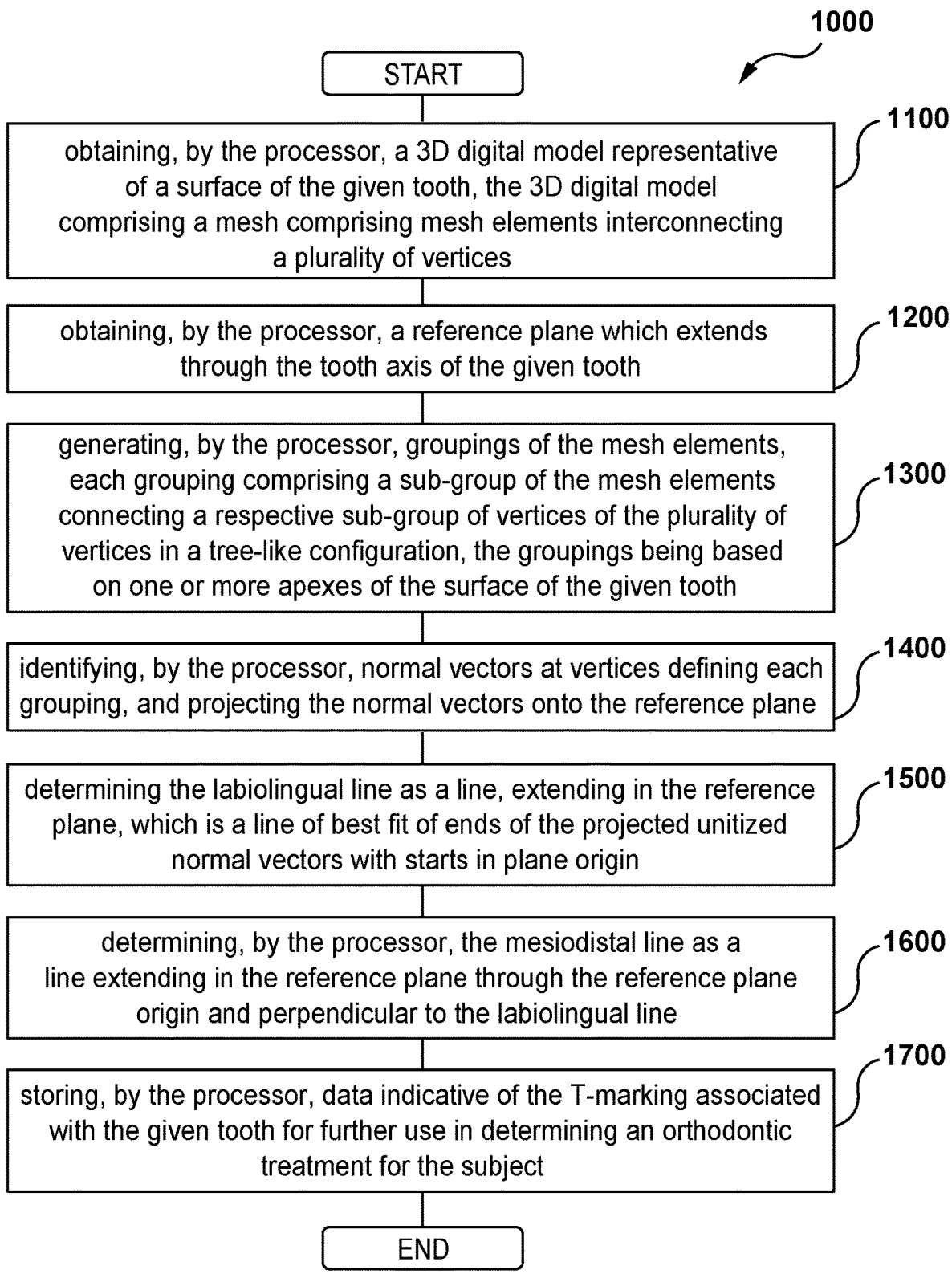
FIG. 10 depicts a flowchart diagram of a method for determining, by a processor of the computing environment of FIG. 9, the T-marking for the given tooth of the subject, in accordance with certain embodiments of the present technology.

With reference to FIG. 10, there is depicted a flowchart of a method 1000 for determining a T-marking, such as the T-marking 700 for a given tooth, such as the given tooth 17, in accordance with certain non-limiting embodiments of the present technology. According to certain non-limiting embodiments of the present technology, the method 1000 can be executed by the processor 950 of the computer system 810.

Step 1100: Obtaining, by the Processor, a 3D Digital Model Representative of a Surface of the Given Tooth, the 3D Digital Model Comprising a Mesh Comprising Mesh Elements Interconnecting a Plurality of Vertices The method 1000 commences at step 1100 with the processor 950 being configured to obtain the image data associated with the subject.

Figure 11:
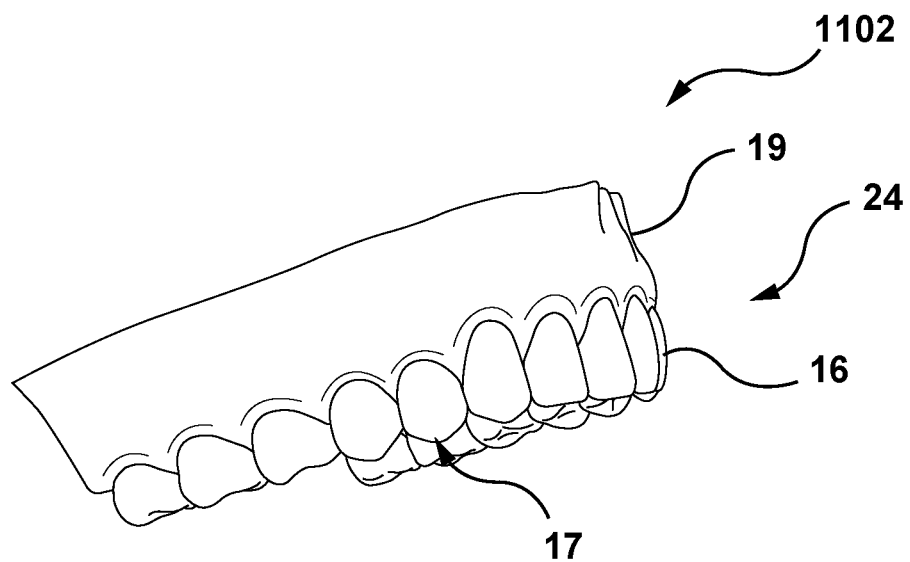
FIG. 11 depicts a perspective view of a 3D digital model of the subject's teeth of FIG. 1, in accordance with certain embodiments of the present technology.
Figure 12:
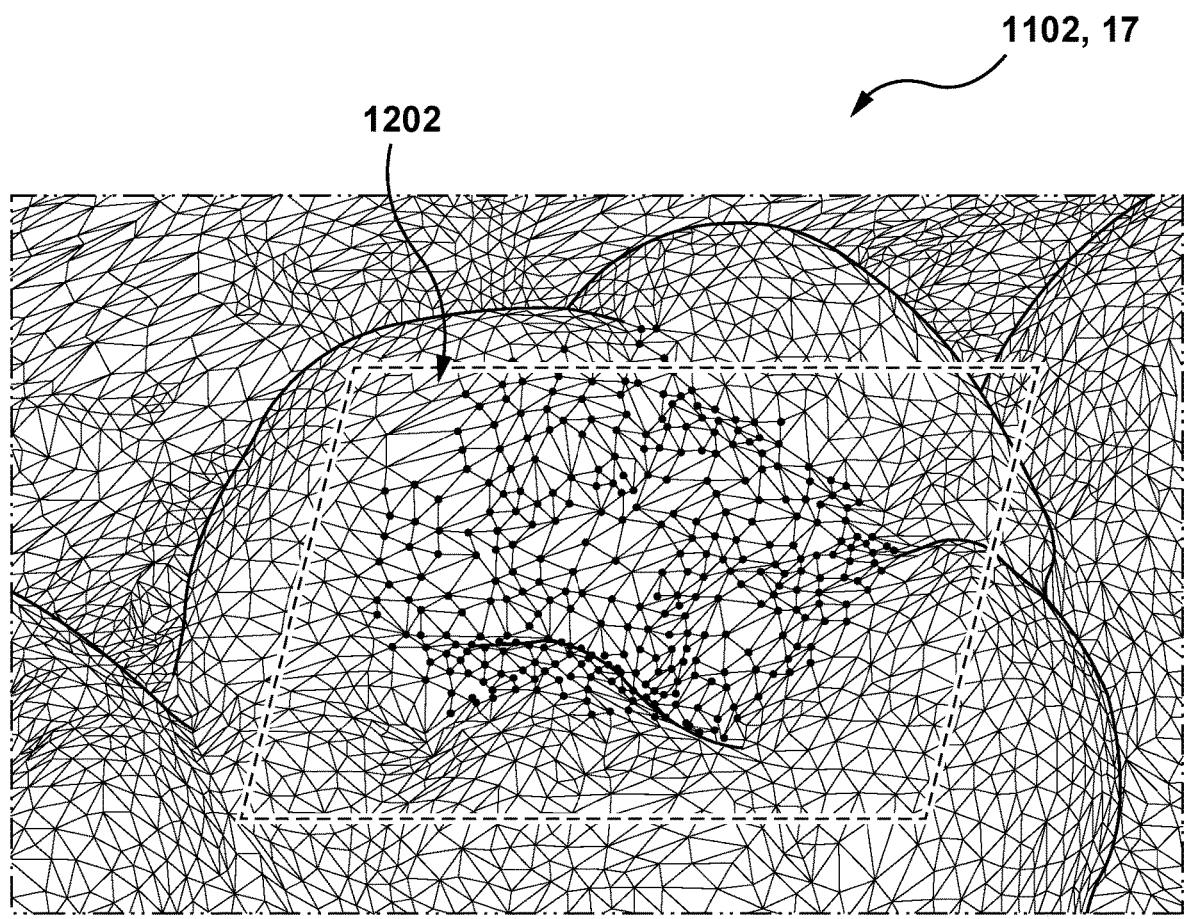
FIG. 12 schematically depicts a reference plane associated with the given tooth of the subject in the 3D digital model of FIG. 11, in accordance with certain non-limiting embodiments of the present technology.

With reference to FIG. 11, there is schematically depicted a perspective view of a 3D digital model 1102 representing the upper arch form 24, which can be used, by the processor 950 for determining the T-marking 700 for the given tooth 17, in accordance with certain non-limiting embodiments of the present technology. In some non-limiting embodiments of the present technology, the 3D digital model 1102 is representative of a surface of the upper teeth 16 (also referred to herein as "maxillary teeth") and the upper gingiva 19 in their current states. However, in other non-limiting embodiments of the present technology, a respective configuration of the 3D digital model 1102 can be representative of desired (or otherwise target) positions of at least some of the upper teeth 16 for a given stage of the orthodontic treatment, such as the desired position 44 of the given one of the upper teeth 16 as described above with reference to FIGS. 5 and 6.

In some non-limiting embodiments of the present technology, the processor 950 can be configured to receive, from the imaging device 830 communicatively coupled with the processor 950, the 3D digital model 1102 comprising a respective plurality of mesh elements (not depicted) representative of the surface of the upper arch form 24. For example, the imaging device 830 can be configured to generate the plurality of mesh elements including, without limitation, triangular mesh elements, quadrilateral mesh elements, convex polygonal mesh elements, or even concave polygonal mesh elements, as an example, without departing from the scope of the present technology.

Needless to say that in certain non-limiting embodiments of the present technology, the processor 950 can be configured to generate a similar 3D digital model indicative of a surface of the lower arch form (not depicted) including lower teeth (also referred to herein as "mandibular teeth") of the subject and a lower gingiva.

The method 1000 hence advances to step 1200.

Step 1200: Obtaining, by the Processor, a Reference Plane which Extends Along an Occlusal Surface of the Given Tooth At step 1200, according to certain non-limiting embodiments of the present technology, using the 3D digital model 1102, the processor 950 can be configured to obtain an indication of a plane along an occlusal surface of the given tooth 17, within which the T-marking 700 is to be constructed, such as a reference plane 1202 depicted in FIG. 12, in accordance with certain non-limiting embodiments of the present technology.

In the context of the present specification, the term "occlusal surface" of a tooth, such as the given tooth 17, denotes a top surface of the crown thereof that, at least partially, comes in contact, or otherwise occludes, with at least one opposing tooth when a mouth of the subject is naturally closed.

In some non-limiting embodiments of the present technology, the processor 950 can be configured to obtain an indication of the reference plane 1202 from an operator of the computer system 810, such as the orthodontic practitioner involved in the planning the orthodontic treatment for the subject. More specifically, the processor 950 can be configured to receive the indication of the reference plane 1202 input over the given tooth 17 in the 3D digital model 1102 using, for example, the mouse 826. In other non-limiting embodiments of the present technology, the reference plane 1202 can be predetermined (such as by a third-party software) for the given tooth 17, and the processor 950 can be configured to receive the indication of the reference plane 1202 in a digital file having been preliminarily created in stored in a format receivable by the computer system 810.

However, in yet other non-limiting embodiments of the present technology, the processor 950 can be configured to determine the reference plane 1202 associated with the given tooth 17. According to certain non-limiting embodiments of the present technology, the processor 950 can be configured to determine the reference plane 1202 as a plane extending through at least some of the vertices defining the occlusal surface of the given tooth 17 in the 3D digital model 1102. For example, the processor 950 can be configured to determine the reference plane 1202 as extending through cusps (not separately numbered) thereof. In another example, the processor 950 can be configured to determine the reference plane 1202 as a plane extending in parallel to a central groove (not separately numbered) of the given tooth 17.

Figure 13:
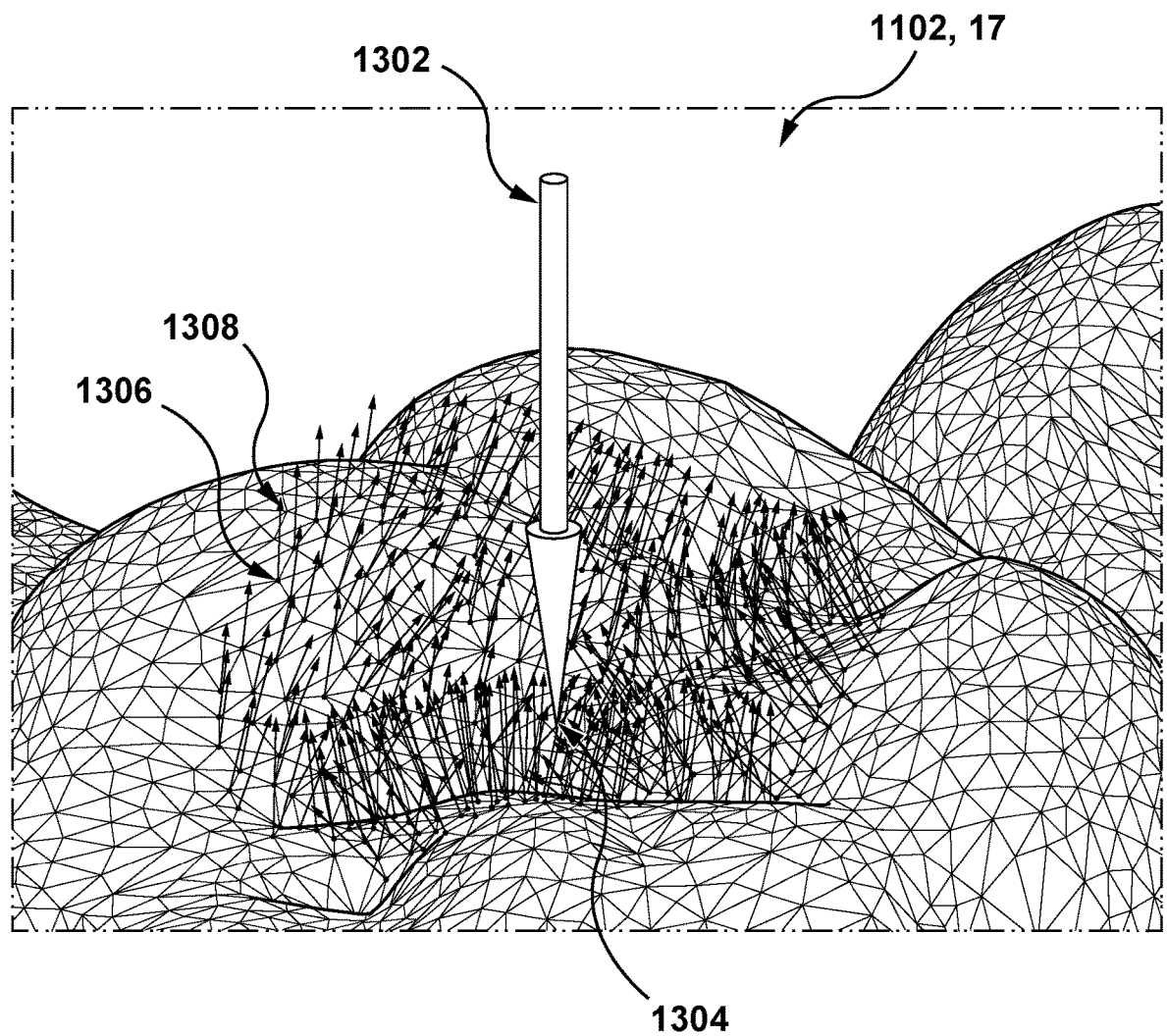
FIG. 13 depicts a schematic diagram for a step of determining, by the processor of the computing environment of FIG. 9, a tooth axis associated with the given tooth in the 3D digital model of FIG. 11, in accordance with certain non-limiting embodiments of the present technology.

However, in some non-limiting embodiments of the present technology, the processor 950 can be configured to determine the reference plane 1202 as a plane extending along the occlusal surface of the given tooth 17 through a longitudinal tooth axis associated therewith, such as a tooth axis 1302 depicted in FIG. 13, in accordance with certain non-limiting embodiments of the present technology. In some non-limiting embodiments of the present technology, the processor 950 can be configured to determine the tooth axis 1302 based on data indicative of specific anatomical features of the crown of the given tooth 17 which includes, without limitation: lobes, developmental grooves, and marginal ridges, as an example.

In some non-limiting embodiments of the present technology, the processor 950 can be configured to determine the tooth axis 1302 associated with the given tooth 17 as an average normal vector of normal vectors determined at vertices defining the occlusal surface of the given tooth 17 in the 3D digital model 1102.

To that end, in some non-limiting embodiments of the present technology, first, the processor 950 can be configured to identify a reference vertex 1304, at which the tooth axis 1302 is to be constructed. According to certain non-limiting embodiments of the present technology, depending on a type (or otherwise identity) of the given tooth 17, the processor 950 can be configured to determine the reference vertex 1304 differently. More specifically, if the given tooth 17 is a premolar or molar, in some non-limiting embodiments of the present technology, the processor 950 can be configured to determine the reference vertex 1304 as corresponding to a geometrical center of the occlusal surface of the given tooth 17. If the given tooth 17 is a canine tooth (not depicted), in some non-limiting embodiments of the present technology, the processor 950 can be configured to determine the reference vertex 1304 as corresponding to a cusp tip of the canine tooth. Further, if the given tooth 17 is an incisor tooth (not depicted), the processor 950 can be configured to determine the reference vertex 1304 as a tip of a central lobe of the incisor tooth.

It is not limited how the processor 950 can be configured to determine the type of the given tooth 17, such as the premolar, molar, canine, or incisor; and in some non-limiting embodiments of the present technology, the processor 950 can be configured to determine the type of the given tooth 17 based on an ordinal number thereof within the upper arch form 24. Also, it should be expressly understood that embodiments where the processor 950 is configured to obtain data of the reference vertex 1304 from the orthodontic practitioner are also envisioned without departing from the scope of the present technology.

Further, in some non-limiting embodiments of the present technology, the processor 950 can be configured to identify occlusal vertices of the occlusal surface of the given tooth 17 around the reference vertex 1304 for determining the tooth axis 1302. In some non-limiting embodiments of the present technology, the processor 950 can be configured to use all the vertices defining the occlusal surface of the given tooth 17 for determining the tooth axis 1302. However, in other non-limiting embodiments of the present technology, the processor 950 can be configured to identify the occlusal vertices as being located around the reference vertex 1304 within a predetermined threshold distance therefrom. For example, in some non-limiting embodiments of the present technology, the predetermined threshold distance can be selected based on a trade-off between an accuracy of determining the tooth axis 1302 and available computational resources of the processor 950, and can comprise, for example, 2, 3, or 5 mm. Additionally, in some non-limiting embodiments of the present technology, the processor 950 can be configured to reduce the number of the occlusal vertices for determining the tooth axis 1302, such as by uniformly filtering thereof. In this regard, the processor 950 can be configured to remove from further consideration, for example, every second, third, or fifth occlusal vertex.

Further, at each of the so identified occlusal vertices, according to certain non-limiting embodiments of the present technology, the processor 950 is configured to determine a respective occlusal normal vector to the occlusal surface of the given tooth 17. For example, at a given occlusal vertex 1306, the processor 950 can be configured to determine an occlusal normal vector 1308. In some non-limiting embodiments of the present technology, each one of the respective occlusal normal vectors associated with the occlusal vertices can have equal magnitudes (lengths) indicating only a respective direction of the normal to the occlusal surface at each one of the occlusal vertices.

Further, by determining the average normal vector of the respective occlusal normal vectors, the processor 950 can be configured to determine a direction for the tooth axis 1302. It is not limited how the processor 550 can be configured to determine the average normal vector, and in some non-limiting embodiments of the present technology, can include: (i) defining, at the reference vertex 1304, a coordinate system, such a three-dimensional Cartesian coordinate system (not depicted); (ii) determine coordinates of each of the respective occlusal normal vectors, determined at each of the occlusal vertices, as mentioned above, in the coordinate system; and (iii) determine coordinates of the average normal vector in the coordinate system as being average coordinates the respective occlusal normal vectors. Further, the processor 950 can be configured to move one end of the so determined average normal vector to the reference vertex 1304, thereby defining the direction for the tooth axis 1302. Further, the processor 950 can be configured to determine the tooth axis 1302 as a line extending in the so determined direction of the average normal vector.

Further, based on the tooth axis 1302, in some non-limiting embodiments of the present technology, the processor 950 can be configured to determine the reference plane 1202. For example, in some non-limiting embodiments of the present technology, the processor 950 can be configured to determine the reference plane 1202 as a plane extending perpendicularly the tooth axis 1302. However, other angles, such as 30, 60, or 75 degrees, for extending the reference plane 1202 through the tooth axis 1302 are also envisioned without departing from the scope of the present technology. In some non-limiting embodiments of the present technology, the processor 950 can be configured to determine the reference plane 1202 as a plane extending through the tooth axis 1302 and originating in the reference vertex 1204.

The method 1000 hence advances to step 1300.

Step 1300: Generating, by the Processor, Groupings of the Mesh Elements, Each Grouping Comprising a Sub-Group of the Mesh Elements Connecting a Respective Sub-Group of Vertices of the Plurality of Vertices in a Tree-Like Configuration, the Groupings being Based on One or More Apices of the Surface of the Given Tooth At step 1300, according to certain non-limiting embodiments of the present technology, using the 3D digital model 1102, the processor 950 can be configured to identify, along the surface of the crown of the given tooth 17, convex portions thereof for determining the T-marking 700 associated with the given tooth 17.

To that end, in some non-limiting embodiments of the present technology, the processor 950 can be configured to identify, along the surface of the crown of the given tooth 17 in the 3D digital model 1102, a plurality of mesh element groupings, each of which is based on a respective apex of the surface of the crown of the given tooth 17, such as one of cusps of the occlusal surface or one of apices of a side surface of the given tooth 17.

According to certain non-limiting embodiments of the present technology, a given mesh element grouping of the plurality of mesh elements groupings can comprise a directional tree extending through respective vertices of the 3D digital model 1102. Broadly speaking, a directional tree is a graphical structure extending through a given mesh, such as the 3D digital model 1102, branches of which comprise edges of the given mesh that are most aligned with a reference direction. For example, in some non-limiting embodiments of the present technology, for the given tooth 17, the reference direction can be selected as being that of the tooth axis 1302 associated with the given tooth 17, determined as described above.

Figure 14:
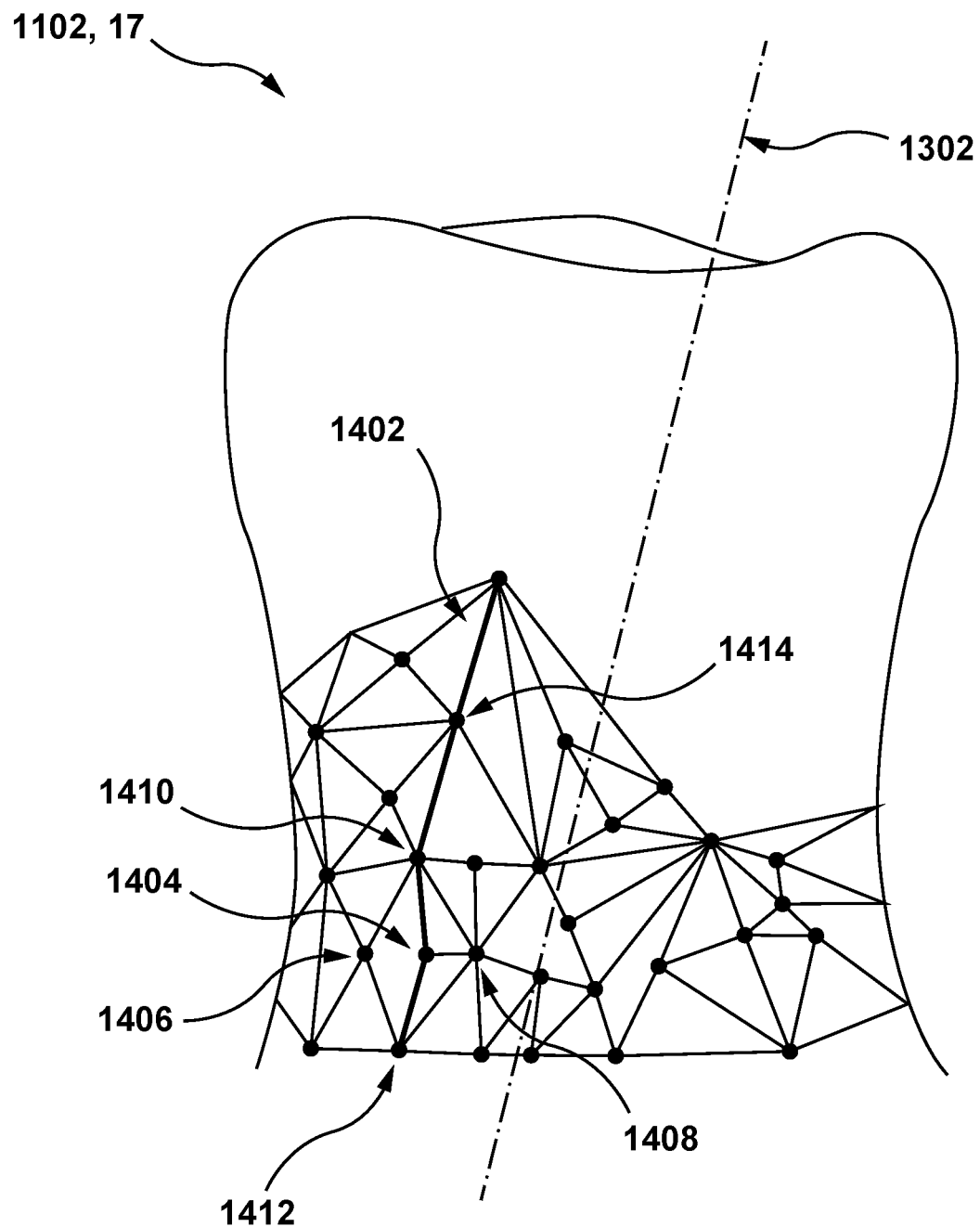
FIG. 14 depicts a schematic diagram for a step of generating, by the processor of the computing environment of FIG. 9, a given grouping of vertices of the 3D digital model along a surface of the given tooth, in accordance with certain non-limiting embodiments of the present technology.

With reference to FIG. 14, there is depicted a schematic diagram for a step of generating, by the processor 950, a given directional tree 1402 along the surface of the given tooth 17 in the 3D digital model 1102 with respect to the tooth axis 1302, in accordance with certain non-limiting embodiments of the present technology.

According to certain non-limiting embodiments of the present technology, to generate the given directional tree 1402, first, the processor 950 can be configured to identify an initial vertex 1404. For example, the processor 950 can be configured to identify the initial vertex 1404 randomly. As it can be appreciated, the initial vertex 1404 has four neighboring vertices: a first neighboring vertex 1406, a second neighboring vertex 1408, a third neighboring vertex 1410, and a fourth neighboring vertex 1412. Further, the processor 950 can be configured to identify a next vertex of the given directional tree 1402, such as one of the first, second, third, and fourth neighboring vertices 1406, 1408, 1410, and 1412 defining an edge of the 3D digital model 1102 that is most aligned with the direction of the tooth axis 1302.

In some non-limiting embodiments of the present technology, the processor 950 can be configured to determine the edge that is most aligned with the direction of the tooth axis 1302 by: (i) projecting each one of the first, second, third, and fourth neighboring vertices 1406, 1408, 1410, and 1412 to the tooth axis 1302; and (ii) determining the edge that is most aligned with the tooth axis 1302 as being one of respective edges connecting the initial vertex 1404 with that one of the first, second, third, and fourth neighboring vertices 1406, 1408, 1410, and 1412, a projection of which is outermost on the tooth axis 1302. However, in other non-limiting embodiments of the present technology, the processor 950 can be configured to: (i) determine a respective angle between each one of the respective edges connecting the initial vertex 1404 with each one of the first, second, third, and fourth neighboring vertices 1406, 1408, 1410, and 1412 and the tooth axis 1302; and (ii) determine the edge that is most aligned with the tooth axis 1302 as that one of the respective edges having a smallest angle with the tooth axis 1302. Thus, for example, the processor 950 can be configured to identify the third neighboring vertex 1410 as defining with the initial vertex 1404 the edge that is most aligned with the direction of the tooth axis 1302. Further, the processor 950 can be configured to traverse the plurality of vertices defining the surface of the given tooth 17 in the 3D digital model 1102 within a predetermined traversal threshold distance, such as 5, 6, or 8 mm around the initial vertex 1404, identifying further next vertices of the given directional tree 1402 from the third neighboring vertex 1410.

It is not limited how the processor 950 can be configured to traverse the plurality of vertices defining the surface of the given tooth 17 in the 3D digital model 1102. For example, in some non-limiting embodiments of the present technology, the processor 950 can be configured to apply a tree traversal search algorithm. In some non-limiting embodiments of the present technology, the tree traversal algorithm may comprise a breadth-first search algorithm. Broadly speaking, the breadth-first search algorithm is a search algorithm configured to search a tree data structure, such as the plurality of vertices defining the surface of the given tooth 17 in the 3D digital model 1102, for a node thereof meeting a predetermined condition—such as a condition of being indicative of the minimum respective pairwise distance in the tree structure. The breadth-first search algorithm is configured to traverse all nodes at a given depth level of the tree data structure first prior to moving to a next depth level. However, it should be noted that in other non-limiting embodiments of the present technology, the implementation of the tree traversal search algorithm is not limited and may include, without limitation, a depth-first search algorithm, an iterative deepening depth-first search algorithm, a parallel breadth-first search algorithm, and others.

Figure 15:
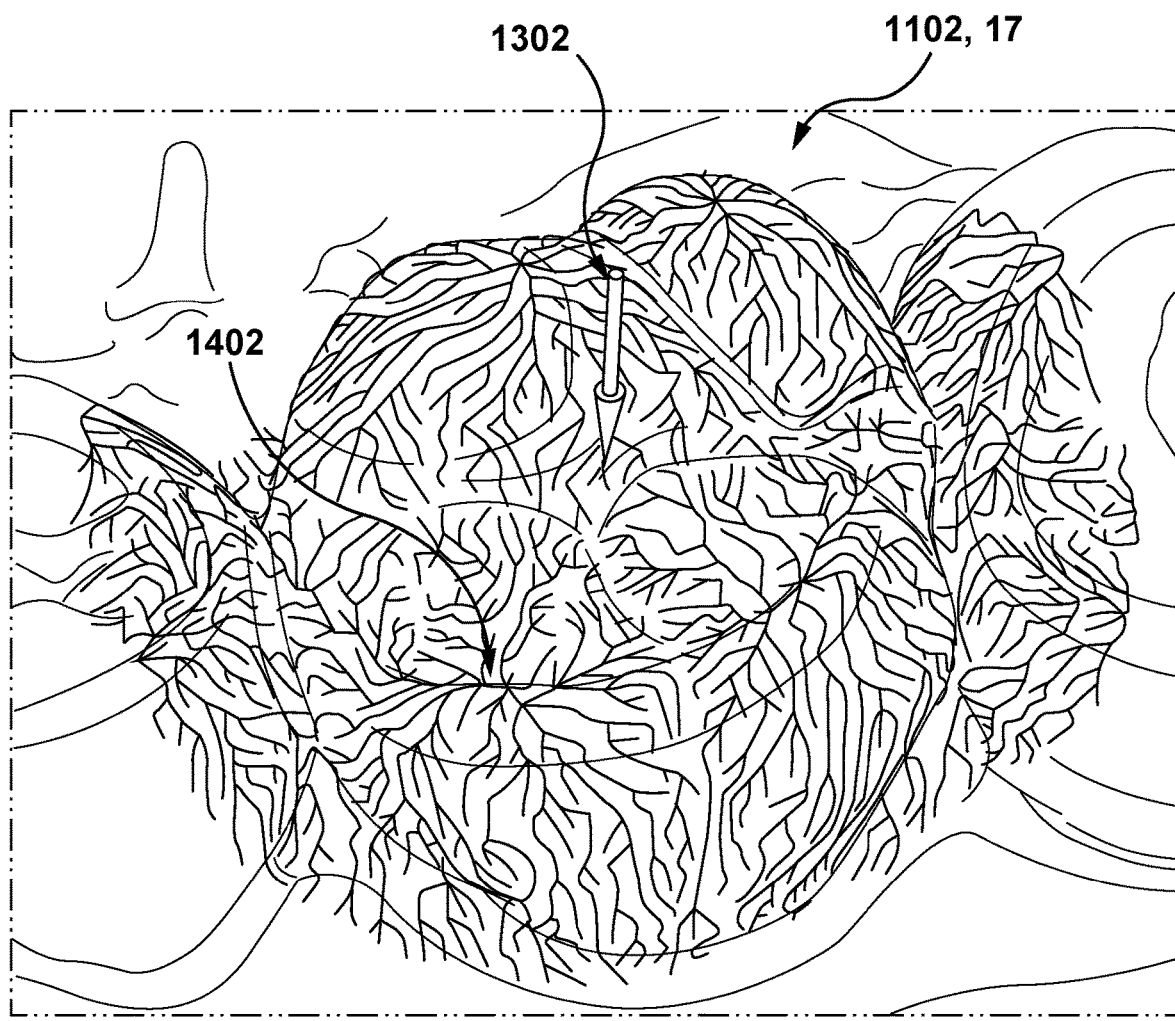
FIG. 15 schematically depicts a plurality of groupings of vertices of the 3D digital model generated, by the processor of the computing environment of FIG. 9, along the surface of the given tooth, in accordance with certain non-limiting embodiments of the present technology.

Further, the processor 950 can be configured to identify other initial vertices for traversing the plurality of vertices defining the surface of the given tooth 17 in the 3D digital model 1102 differently, generating other directional trees. Thus, by doing so, the processor 950 can be configured to generate a plurality of directional trees along the surface of the given tooth 17 in the 3D digital model 1102, as schematically depicted in FIG. 15, in accordance with certain non-limiting embodiments of the present technology. As it can be appreciated, the processor 950 can be configured to identify the plurality of directional trees as being directional trees, branches of which do not intersect.

Further, in some non-limiting embodiments of the present technology, the processor 950 can be configured to filter the plurality of so generated directional trees to identify only directional trees extending along the surface of the given tooth 17 in the 3D digital model 1102. To that end, in some non-limiting embodiments of the present technology, first, the processor 950 can be configured to: (i) identify, in the plurality of directional trees, those directional trees whose apices (relative to a surface of the 3D digital model 1102) are located at more than a predetermined threshold distance away from the reference vertex 1304; and (ii) remove such directional trees from further consideration. For example, the predetermined threshold distance can be selected to be 5, 6, 8, or 10 mm. In other non-limiting embodiments of the present technology, instead of filtering out entire directional trees, the processor 950 can be configured to identify only vertices of the plurality of directional trees that are located more than the predetermined threshold distance away from the reference vertex 1304, and remove these vertices from further consideration.

Further, in some non-limiting embodiments of the present technology, the processor 950 can be configured to: (i) identify, in the plurality of directional trees, those directional trees having a number of vertices that is less than a predetermined threshold vertex number, which depending on various non-limiting embodiments of the present technology, can be 30, 40, or 80, for example; and (ii) remove such directional trees from further consideration.

Figure 16:
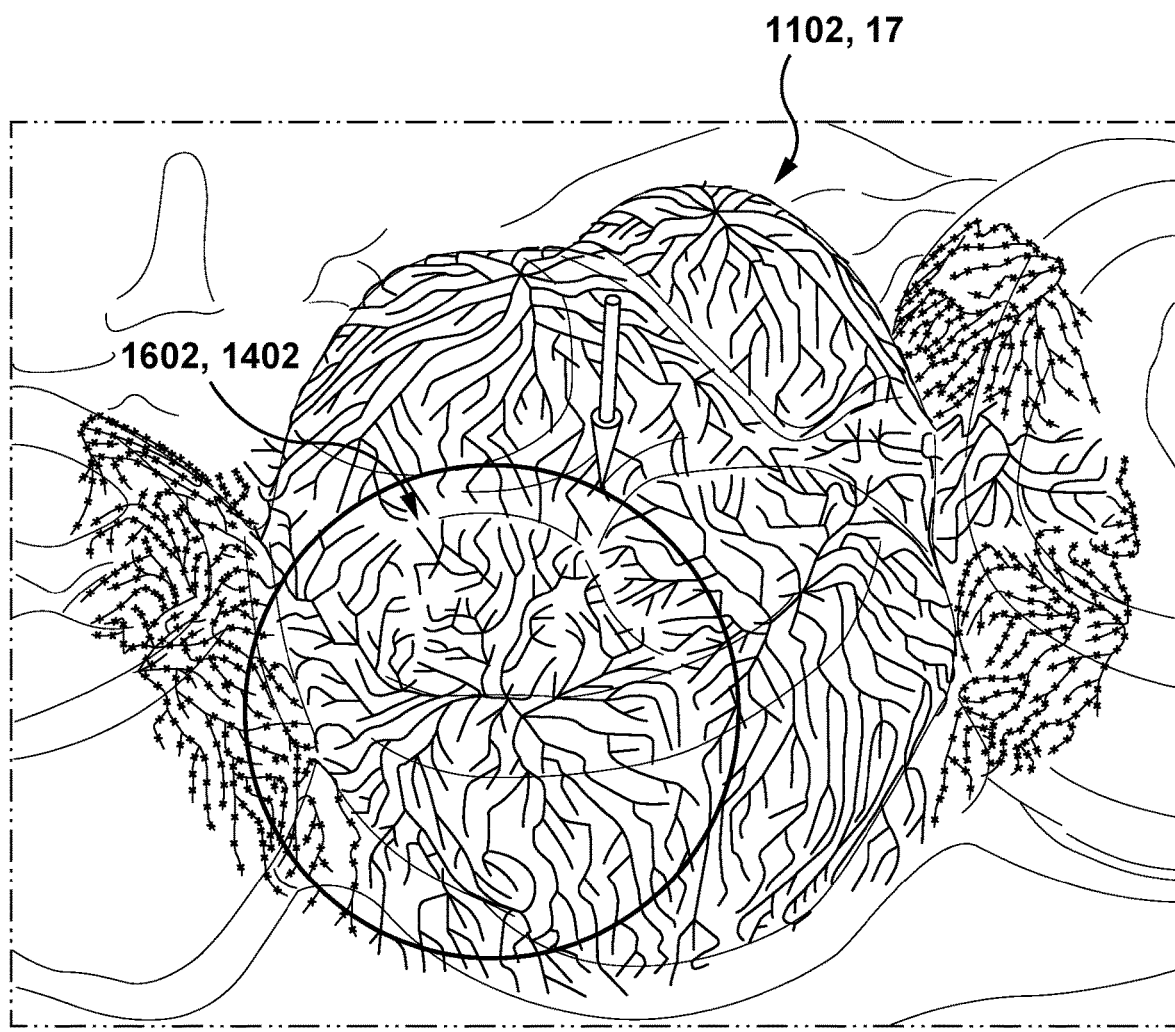
FIG. 16 depicts a schematic diagram for a step of filtering, by the processor of the computing environment of FIG. 9, the plurality of grouping of vertices of FIG. 15, in accordance with certain non-limiting embodiments of the present technology.

In some non-limiting embodiments of the present technology, the processor 950 can be configured to remove those directional trees that have comparatively small "crowns". To that end, in some non-limiting embodiments of the present technology, the processor 950 can be configured to fit each one of the plurality of directional trees to a sphere, such as the given directional tree 1402 to a respective fit sphere 1602, as schematically depicted in FIG. 16, in accordance with certain non-limiting embodiments of the present technology.

According to certain non-limiting embodiments of the present technology, the processor 950 can be configured to generate the respective fit sphere 1602 around the given directional tree 1402 such that a sum of distance values from each vertex defining the given directional tree 1402 to a surface of the respective fit sphere 1602 is minimized. To that end, the processor 950 can be configured to apply a fitting algorithm, including, for example, a linear or non-linear regression algorithm, using, for example, a least square method.

Further, based on dimensions and a position of the respective fit sphere 1602, the processor 950 can be configured to determine whether keep or disregard the given directional tree 1402. More specifically, in some non-limiting embodiments of the present technology, the processor 950 can be configured to remove the given directional tree 1402 from further consideration if the respective fit sphere 1602 thereof does not intersect the tooth axis 1302. In other non-limiting embodiments of the present technology, the processor 950 can be configured to remove the given directional tree 1402 from further consideration if the respective fit sphere 1602 is located more than a second predetermined threshold distance, such as 5, 6, or 8 mm, away from the tooth axis 1302. In yet other non-limiting embodiments of the present technology, the processor 950 can be configured to remove the given directional tree 1402 from further consideration if a radius of the respective fit sphere 1602 is greater than a predetermined radius threshold, such as 6 mm, for example.

In some non-limiting embodiments of the present technology, the processor 950 can be configured to filter out the plurality of directional trees based on respective fit spheres thereof as described above only if the given tooth 17 is of one of predetermined types of teeth, such as one of a premolar and molar, as an example. It is not limited how the processor 950 can be configured to determine the type of the given tooth 17, and in some non-limiting embodiments of the present technology, can comprise determining the type based on the ordinal number of the given tooth 17 within the upper arch form 24 as mentioned above.

Figure 17A:
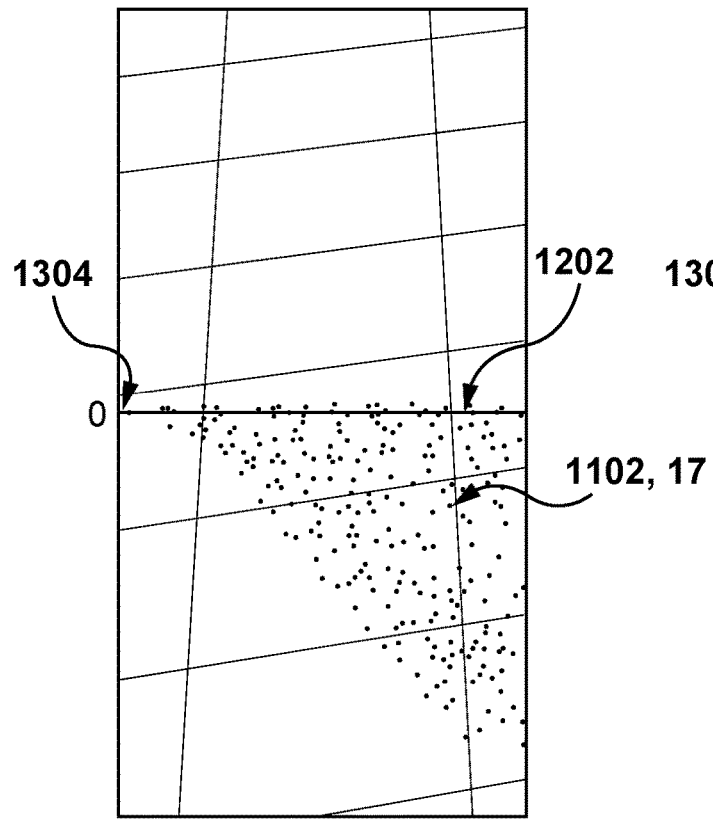
FIGS. 17A and 17B depict lingual side views of vertices of the 3D digital model of FIG. 11 representative of occlusal surfaces of different types of the subject's teeth, in accordance with certain non-limiting embodiments of the present technology.

However, in other non-limiting embodiments of the present technology, the processor 950 can be configured to determine the type of the given tooth 17 differently. More specifically, with back reference to FIG. 13, in some non-limiting embodiments of the present technology, the processor 950 can be configured to analyze a distribution of the occlusal vertices relative to the reference plane 1202, determined as extending perpendicular to the tooth axis 1302 and originating in the reference vertex 1304, as mentioned above. Thus, if more than a predetermined portion, such as 75%, 80%, or 90%, of the occlusal vertices are located between the reference plane 1202 and the surface of the upper gingiva 19 (that is, under the reference plane 1202 in the orientation of FIG. 13), the processor 950 can be configured to determine the given tooth 17 as being one of a canine and an incisor. For example, FIG. 17A schematically depicts a lingual view of the occlusal vertices of the given tooth 17, in accordance with certain non-limiting embodiments of the present technology, where more than the predetermined portion of the occlusal vertices are disposed between the reference plane 1202 and the surface of the upper gingiva 19 (not depicted in FIG. 17A), in which case the processor 950 can be configured to determine the given tooth 17 as being one of the canine or incisor.

Figure 17B:
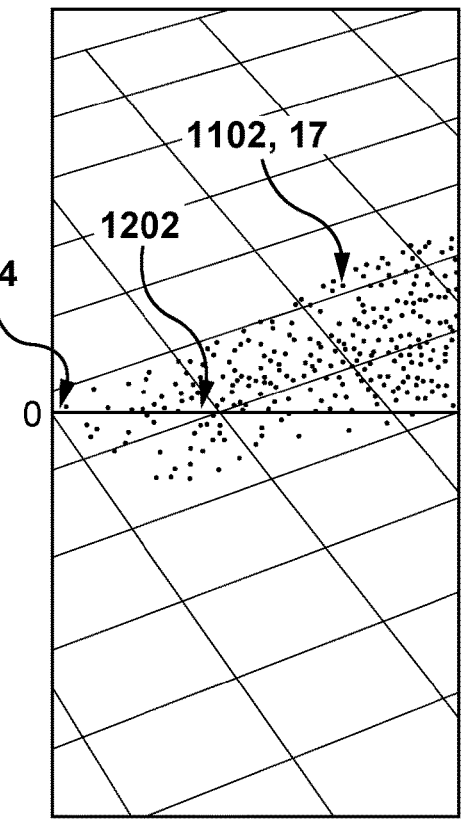

By contrast, if less than the predetermined portion of the occlusal vertices are located between the reference plane 1202 and the surface of the upper gingiva 19 in the 3D digital model 1102, as schematically depicted in FIG. 17B, in accordance with certain non-limiting embodiments of the present technology, the processor 950 can be configured to determine the given tooth 17 as being one of a premolar and a molar.

Alternatively or additionally to the filtering approaches described above, the processor 950 can be configured to remove a predetermined portion, such as 5%, 10%, or 20%, of the vertices defining the given directional tree 1402. In some non-limiting embodiments of the present technology, the processor 950 can be configured to determine each one of the predetermined portion of vertices randomly. In other non-limiting embodiments of the present technology, the processor 950 can be configured to determine the predetermined portion of vertices to be removed as uniformly distributed along the given directional tree 1402.

The method 1000 hence advances to step 1400.

Step 1400: Identifying, by the Processor, Normal Vectors at Vertices Defining Each Grouping, and Projecting the Normal Vectors onto the Reference Plane At step 1400, according to certain non-limiting embodiments of the present technology, the processor 950 can be configured to use the plurality of directional trees identified and filtered as described at step 1300 to identify along the surface of the given tooth 17 convex portions thereof for further determining the T-marking 700.

Figure 18:
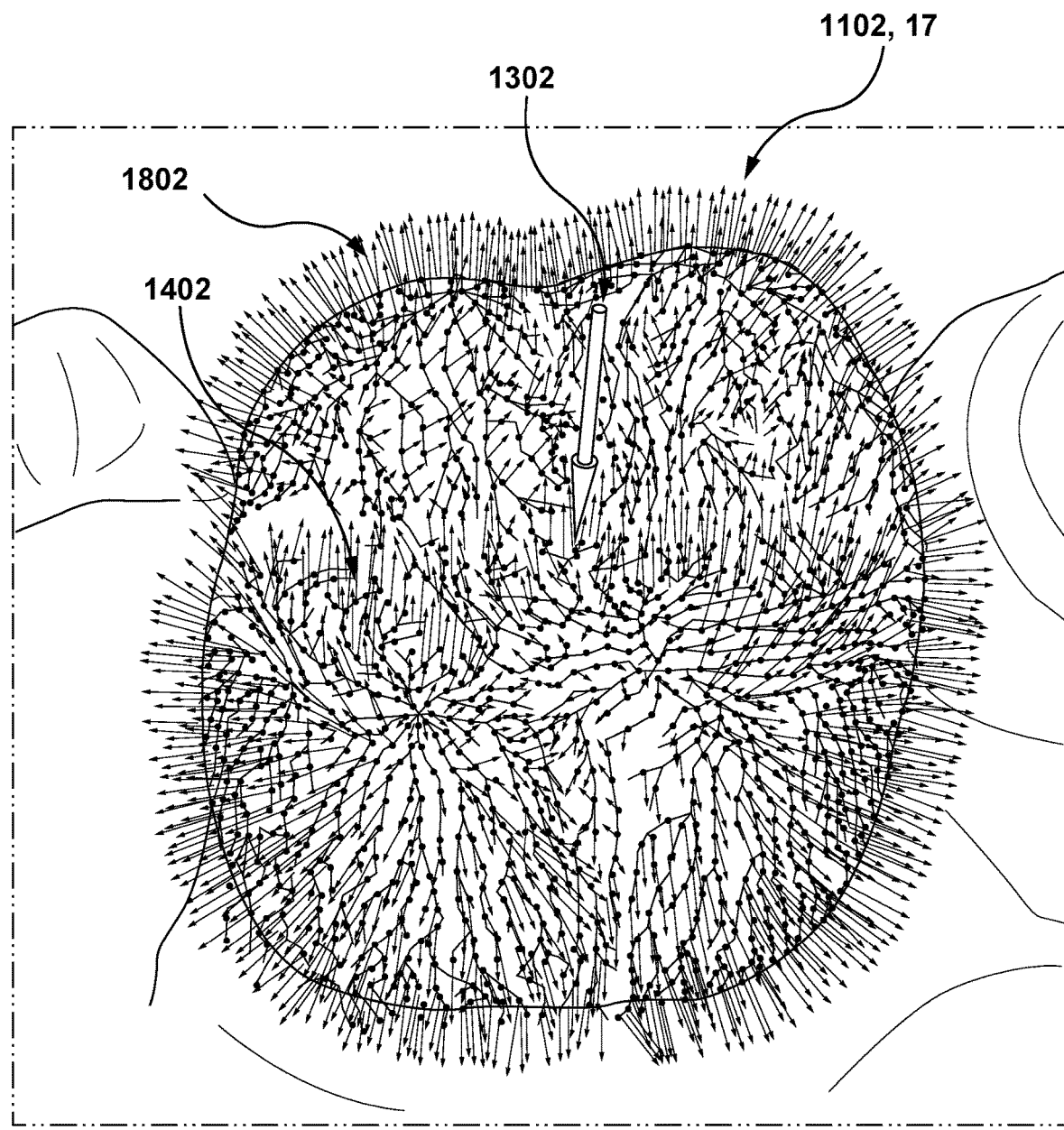
FIG. 18 schematically depicts normal vectors determined, by the processor of the computing environment of FIG. 9, at vertices of the 3D digital model of FIG. 11 defining the plurality of groupings of vertices of FIG. 15, in accordance with certain non-limiting embodiments of the present technology.

More specifically, according to certain non-limiting embodiments of the present technology, the processor 950 can be configured to determine, at each vertex defining the plurality of directional trees, a respective normal vector to the surface of the given tooth 17, as schematically depicted in FIG. 18, according to certain non-limiting embodiments of the present technology. Thus, the processor 950 can be configured to generate a plurality of normal vectors 1802. Similar to the occlusal normal vectors mentioned above at step 1200, each one of the plurality of normal vectors 1802 can have an equal length, indicative only a respective normal direction at a given vertex of the plurality of directional trees.

Figure 19:
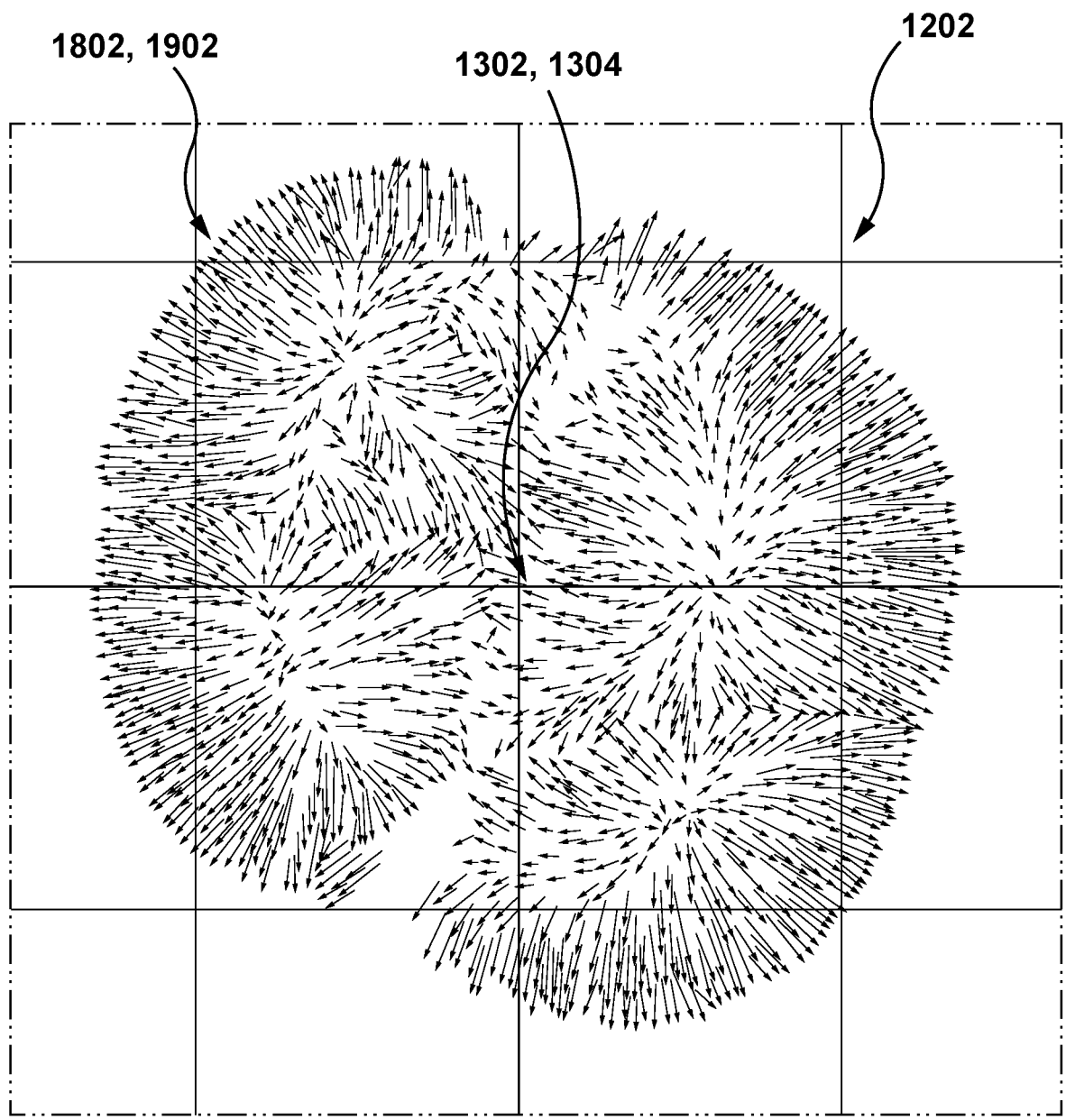
FIG. 19 schematically depicts the normal vectors of FIG. 18 projected, by the processor of the computing environment of FIG. 9, onto the reference plane of FIG. 12, in accordance with certain non-limiting embodiments of the present technology.

Further, in some non-limiting embodiments of the present technology, the processor 950 can be configured to project each one of the plurality of normal vectors 1802 onto the reference plane 1202 determined as described above at step 1200. Thus, the processor 950 can be configured to generate a plurality of projected normal vectors 1902 as schematically depicted in FIG. 19 illustrating a top view of the reference plane 1202, in accordance with certain non-limiting embodiments of the present technology.

In some non-limiting embodiments of the present technology, after projecting the plurality of normal vectors 1802 onto the reference plane 1202, the processor 950 can be configured to unitize each one of the plurality of projected normal vectors 1902, that is, assign thereto an equal length, such as a unit length.

The method 1000 thus proceeds to step 1500.

Figure 20:
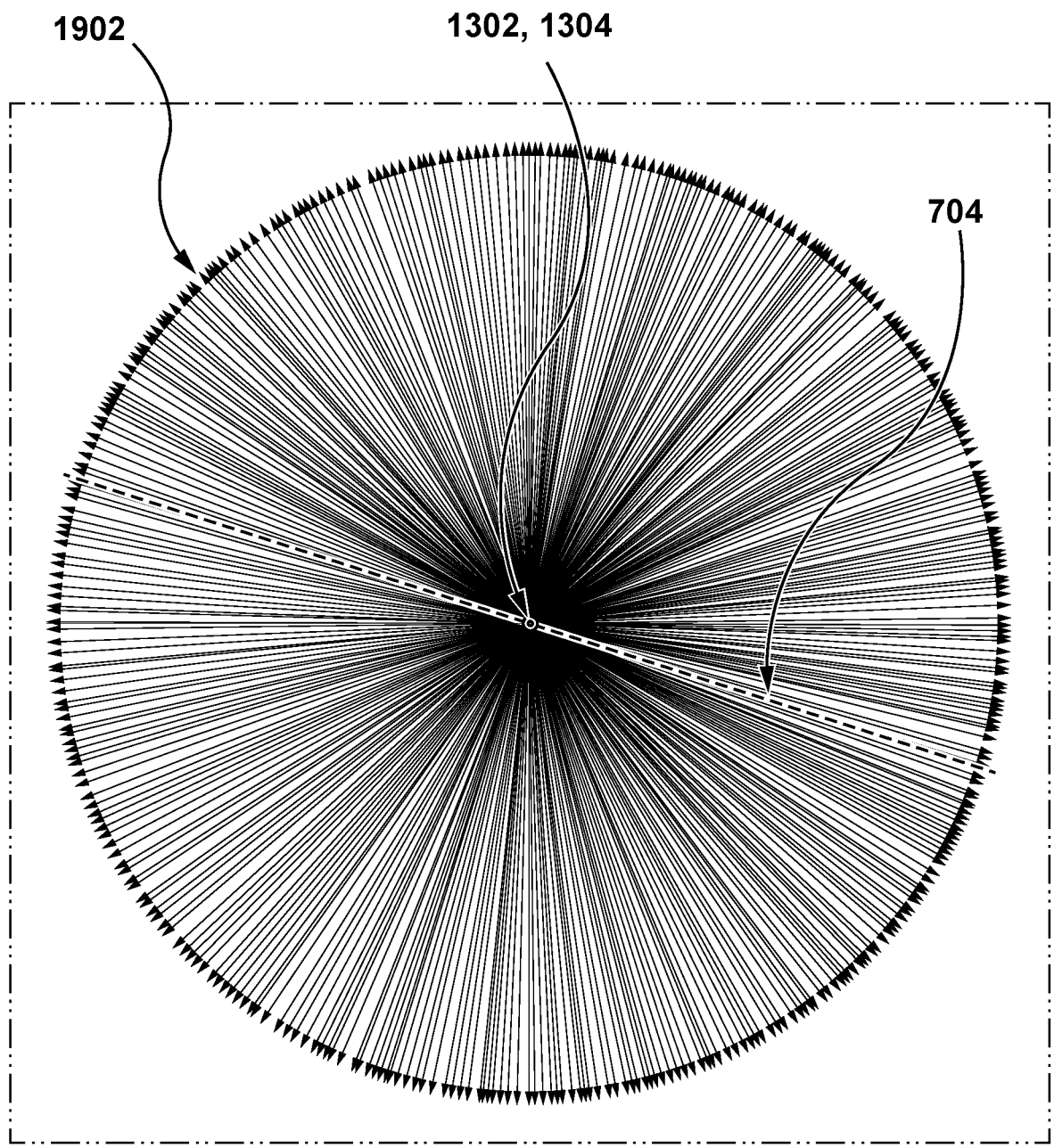
FIG. 20 depicts a schematic diagram for a step of determining a labiolingual line of the T-marking associated with the given tooth based on the projected normal vectors of FIG. 19, in accordance with certain non-limiting embodiments of the present technology.

Step 1500: Determining the Labiolingual Line as a Line, Extending in the Reference Plane, which is a Line of Best Fit of Ends of the Projected Unitized Normal Vectors with Starts in Plane Origin Further, based on the plurality of projected normal vectors 1902, the processor 950 can be configured to determine the labiolingual line 704 of the T-marking 700 associated with the given tooth 17. To that end, according to certain non-limiting embodiments of the present technology, the processor 950 can be configured to move origins of each one of the plurality of projected normal vectors 1902 within the reference plane 1202 to the reference vertex 1304. Thus, ends of the plurality of projected normal vectors 1902 so rearranged within the reference plane 1202 define a circle with a center at the reference vertex 1304, as schematically depicted in FIG. 20, in accordance with certain non-limiting embodiments of the present technology.

In some non-limiting embodiments of the present technology, the processor 950 can be configured to determine the labiolingual line 704 as a line of best fit of the ends of the plurality of projected normal vectors 1902 arranged in the circle as described above. More specifically, in these embodiments, the processor 950 can be configured to determine the labiolingual line 704 of the T-marking 700 as a line, from which a sum of distance values to the ends of the plurality of projected normal vectors 1902, with the origins thereof displaced to the reference vertex 1304, is minimized.

In other non-limiting embodiments of the present technology (not depicted), to determine the labiolingual line 704, the processor 950 can be configured to: (i) analyze the plurality of projected normal vectors 1902 within the reference plane 1202 without the rearrangement of the ends thereof in the circle; (ii) generate a density field of the ends of the plurality of projected normal vectors 1902 within the reference plane 1202; and (iii) determine the labiolingual line 704 as a weighted line of best fit of local maxima of the density field.

The method 1000 hence advances to step 1600.

Step 1600: Determining, by the Processor, the Mesiodistal Line as a Line Extending in the Reference Plane Through the Reference Plane Origin and Perpendicular to the Labiolingual Line; Determining, by the Processor, the T-Marking of the Given Tooth as the Labiolingual Line Intersecting the Mesiodistal Line At step 1600, according to certain non-limiting embodiments of the present technology, the processor 950 can be configured to determine the mesiodistal line 702 of the T-marking 700 as a line extending from the reference vertex 1304 in the reference plane 1202 perpendicular to the labiolingual line 704 determined at step 1500.

Figure 21:
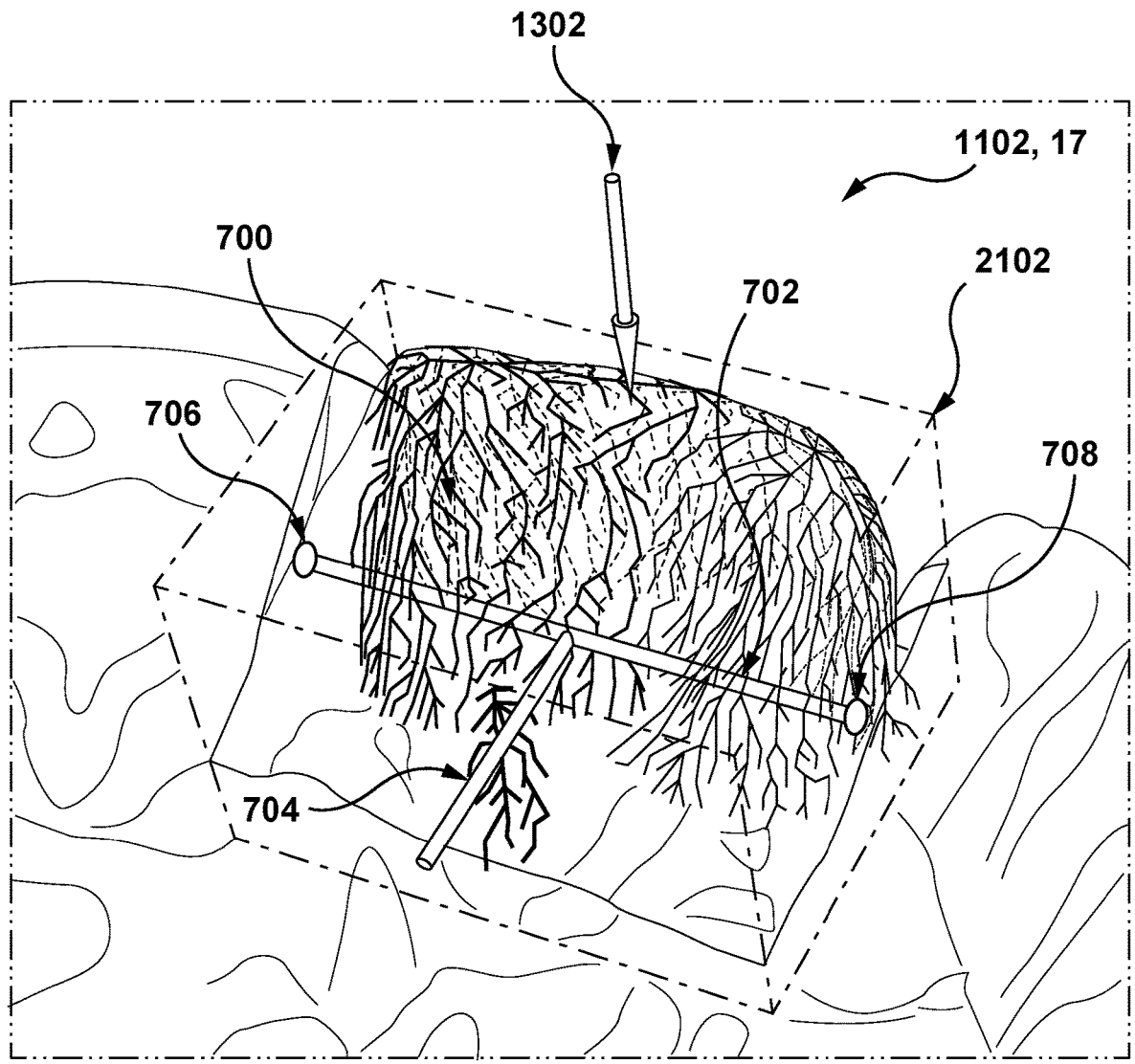
FIG. 21 depicts a schematic diagram for a step of determining a mesiodistal line of the T-marking associated with the given tooth and further truncating each one of the mesiodistal and labiolingual lines.

Further, in some non-limiting embodiments of the present technology, the processor 950 can be configured to truncate the mesiodistal and labiolingual lines 702, 704 to dimensions of the crown of the given tooth 17. To that end, as schematically depicted in FIG. 21, in accordance with certain non-limiting embodiments of the present technology, the processor 950 can be configured to generate around the plurality of directional trees, a bounding box 2102.

In the context of the present specification, a bounding box, such as the bounding box 2102, denotes a three-dimensional box (or a parallelepiped) of a smallest possible measure (such as an area or a volume thereof) allowing for entirely enclosing a given point set, such as vertices if the plurality of directional trees extending along the surface of the given tooth 17 in the 3D digital model 1102.

Thus, in some non-limiting embodiments of the present technology, the processor 950 can be configured to determine the T-marking 700 as intersecting segments of the mesiodistal and labiolingual lines 702, 704 enclosed in the bounding box 2102. In some non-limiting embodiments of the present technology, the processor 950 can further be configured to truncate a labial portion of the labiolingual line 704, that is, the portion extending from the reference vertex 1304 in a labial direction. Thus, the processor 950 can be configured to determine the T-marking 700 associated with the given tooth 17, as schematically depicted in FIG. 21, in accordance with certain non-limiting embodiments of the present technology. In some non-limiting embodiments of the present technology, the processor 950 can further be configured to determine positions of the mesial and distal points 706, 708 associated with the given tooth 17 as points of intersection of the mesiodistal line 702 with the bounding box 2102.

In some non-limiting embodiments of the present technology, the processor 950 can be configured to modulate a position of the T-marking 700 within the given tooth 17 in the 3D digital model 1102, for example, by vertically translating the reference plane 1202 with the T-marking 700 defined therein. In some non-limiting embodiments of the present technology, the processor 950 can be configured to translate the reference plane 1202 such that origins of the respective T-markings associated with each one of the upper teeth 16 are at the same level.

The method 1000 hence advances to step 1700.

Step 1700: Storing, by the Processor, Data Indicative of the T-Marking Associated with the Given Tooth for Further Use in Determining an Orthodontic Treatment for the Subject At step 1700, according to certain non-limiting embodiments of the present technology, the processor 950 can be configured to store data of the T-marking 700 associated with the given tooth 17, determined as described above, in a memory of the computer system 810, such as the solid-state drive 960.

Further, the processor 950 can be configured to use one of the applications of the T-marking 700 non-exhaustively listed above for determining the orthodontic treatment for the subject. For example, using the T-marking 700, the processor 950 can be configured to determine tooth movements required to cause the given tooth 17 to move from the initial position 42 to the desired position 44, as mentioned above. Further, based on the required tooth movements, the processor 950 can be configured to determine forces to be applied to the given tooth 17 in the course of the orthodontic treatment to cause the given tooth 17 to perform the tooth movement towards the desired position 44. To that end, as mentioned above, to determine the forces at each step of the orthodontic treatment, the processor 950 can apply one of the approaches described in one of the co-owned U.S. Pat. Nos. 10,993,782-B1 and 11,259,897-B1.

Further, based on the mesial and distal points 706, 708 associated with the given tooth 17, the processor 950 can be configured to determine application points for forces causing the given tooth 17 to move towards the desired position 44. Finally, based on the so determined forces to be applied at respective steps of the orthodontic treatment and application points, the processor 950 can be configured to cause manufacture of one of the implementations of the orthodontic appliance 10, such as one of the bracket/archwire systems 10a and the aligner system 10b.

The method 1000 hence terminates.

Thus, certain embodiments of the method 1000 allow determining the respective T-markings, and hence the mesial and distal points, for each one of the subject's teeth consistently, which may help minimize the human error and translate to a more accurate planning of orthodontic treatments for subjects.

It should be expressly understood that not all technical effects mentioned herein need to be enjoyed in each and every embodiment of the present technology.

Modifications and improvements to the above-described implementations of the present technology may become apparent to those skilled in the art. The foregoing description is intended to providing examples of implementations of the present technology rather than being limiting. The scope of the present technology is therefore intended to be limited solely by the scope of the appended claims.

The invention claimed is:

1. A method for determining a T-marking of a given tooth of a subject, the T-marking including a labiolingual line and a mesiodistal line, the method being executable by a processor, the method comprising:
   obtaining, by the processor, a 3D digital model representative of a surface of a plurality of subject's teeth including the given tooth, the 3D digital model comprising a mesh comprising mesh elements interconnecting a plurality of vertices;
   obtaining, by the processor, a reference plane which extends along an occlusal surface of the given tooth;
   generating, by the processor, groupings of the mesh elements, each grouping comprising a sub-group of the mesh elements connecting a respective sub-group of vertices of the plurality of vertices in a tree-like configuration, the groupings being based on one or more apices of the surface of the given tooth;
   identifying, by the processor, normal vectors at vertices defining each grouping, and projecting the normal vectors onto the reference plane;
   determining the labiolingual line as a line, extending in the reference plane, which is a line of best fit of ends of the projected unitized normal vectors with starts in plane origin;
   determining, by the processor, the mesiodistal line as a line extending in the reference plane through the reference plane origin and perpendicular to the labiolingual line;
   determining, by the processor, the T-marking of the given tooth as the labiolingual line intersecting the mesiodistal line; and
   storing, by the processor, data indicative of the T-marking associated with the given tooth for further use in determining an orthodontic treatment for the subject.

2. The method of claim 1, further comprising, after the projecting the normal vectors onto the reference plane, moving an origin of each of the normal vectors to a reference vertex on an occlusal surface of the given tooth, and wherein the determining the line of best fit comprises determining the line of best fit with respect to the origins.

3. The method of claim 1, wherein the generating a given grouping comprises:
   obtaining, by the processor, data of a tooth axis associated with the given tooth; and
   identifying, by the processor, edges of the mesh that are most aligned with the tooth axis associated with the given tooth when traversing the plurality of vertices representative of the given tooth.

4. The method of claim 3, wherein the identifying the edges most aligned with the direction of the tooth axis comprises:
   identifying, by the processor, a given vertex associated with the given tooth;
   identifying, by the processor, a set of neighboring vertices of the given vertex, each one of the set of neighboring vertex being connected to the given vertex through a respective edge;
   projecting, by the processor, each one of the set of neighboring vertices on the tooth axis of the given tooth; and
   determining, by the processor, a given most aligned edge from the given vertex as the respective edge that connects the given vertex with that one of the set of neighboring vertices, a projection of which on the tooth axis is outermost on the tooth axis.

5. The method of claim 3, wherein the generating the groupings comprises generating the groupings from vertices within a predetermined distance from a reference point on an occlusal surface of the given tooth.

6. The method of claim 1, further comprising:
determining if at least one vertex of a given grouping is located more than a predetermined distance, along the surface of the given tooth, from a reference point on an occlusal surface of the given tooth; and
in response to determining that the at least one vertex of the given grouping is located more than the predetermined distance from the reference vertex, removing the at least one vertex of the given grouping from further consideration.

7. The method of claim 1, further comprising omitting a given grouping from further consideration if it has less than a predetermined number of vertices.

8. The method of claim 1, wherein the method further comprises fitting a sphere to a given grouping by minimizing a sum of distances from the vertices of the grouping to a surface of the sphere, and omitting a given grouping from further consideration if one or more of the following apply:
(i) the fit sphere does not intersect a tooth axis of the given tooth;
(ii) the fit sphere has a radius of more than a predetermined threshold radius; and
(iii) a center of the fit sphere is more than a predetermined distance from the tooth axis of the given tooth.

9. The method of claim 8, wherein the fitting the sphere is performed if the given tooth is identified as a molar, premolar or a canine tooth.

10. The method of claim 9, further comprising determining an identity of the given tooth, the determining comprising:
identifying, by the processor, in the 3D digital model, occlusal vertices representative of the occlusal surface of the given tooth;
separating the occlusal vertices using the reference plane;
determining, by the processor, that the given tooth is a molar or premolar tooth if more than a predetermined portion of the occlusal vertices lie between the reference plane and a surface of a gingiva around the given tooth; and
determining, by the processor, that the given tooth is a incisor or canine tooth if less than the predetermined portion of the occlusal vertices lie between the reference plane and the surface of the gingiva around the given tooth.

11. The method of claim 1, further comprising reducing a complexity of the mesh of the 3D digital model, before generating the groupings, by removing mesh elements whilst retaining the vertices.

12. The method of claim 1, further comprising, for each grouping, randomly removing one or more vertices.

13. The method of claim 1, further comprising obtaining data of a tooth axis associated with the given tooth, and wherein the obtaining the reference plane comprises obtaining the reference plane such that the reference plane extends through the tooth axis associated with the given tooth.

14. The method of claim 12, wherein the obtaining the data of the tooth axis comprises determining, by the processor, the tooth axis of the given tooth, the determining the tooth axis comprising:
identifying a reference vertex on an occlusal surface of the given tooth;
identifying occlusal vertices of the plurality of vertices which are within a predetermined distance from the reference vertex;
determining a normal vector for each of the occlusal vertices;
determining an average normal vector for the occlusal vertices, and
determining the tooth axis of the given tooth as extending in a direction of the determined average normal vector through the reference vertex.

15. The method of claim 12, wherein the reference vertex is selected at a geometrical center of the occlusal surface.

16. The method of claim 1, wherein the determining the mesiodistal line comprises building a bounding box around the groupings; and using the bounding box to truncate the mesiodistal line to dimensions of the given tooth.

17. An electronic device for determining a T-marking of a given tooth of a subject, the T-marking including a labiolingual line and a mesiodistal line, the electronic device comprising a processor and a non-transitory computer-readable medium storing instructions; and the processor, upon executing the instructions, being configured to:
obtain a 3D digital model representative of a surface of a plurality of subject's teeth including the given tooth, the 3D digital model comprising a mesh comprising mesh elements interconnecting a plurality of vertices;
obtain a reference plane which extends along an occlusal surface of the given tooth;
generate groupings of the mesh elements, each grouping comprising a sub-group of the mesh elements connecting a respective sub-group of vertices of the plurality of vertices in a tree-like configuration, the groupings being based on one or more apices of the surface of the given tooth;
identify normal vectors at vertices defining each grouping, and projecting the normal vectors onto the reference plane;
determine the labiolingual line as a line, extending in the reference plane, which is a line of best fit of ends of the projected unitized normal vectors with starts in plane origin;
determine the mesiodistal line as a line extending in the reference plane through the reference plane origin and perpendicular to the labiolingual line;
determine the T-marking of the given tooth as the labiolingual line intersecting the mesiodistal line; and
store data indicative of the T-marking associated with the given tooth for further use in determining an orthodontic treatment for the subject.

18. The electronic device of claim 17, wherein after projecting the normal vectors onto the reference plane, the processor is further configured to move an origin of each of the normal vectors to a reference vertex on an occlusal surface of the given tooth, and determine the line of best fit with respect to the origins.

19. The electronic device of claim 17, wherein to generate a given grouping, the processor is configured to identify edges of the mesh that are most aligned with the tooth axis associated with the given tooth when traversing the plurality of vertices representative of the given tooth along the tooth axis thereof.

20. The electronic device of claim 19, wherein to identify the edges most aligned with the direction of the tooth axis, the processor is configured to:
identify a given vertex of the plurality of vertices associated with the given tooth;

identify a set of neighboring vertices of the given vertex, each one of the set of neighboring vertex being connected to the given vertex through a respective edge;

project each one of the set of neighboring vertices on the tooth axis of the given tooth; and determine a given most aligned edge from the given vertex as the respective edge that connects the given vertex with that one of the set of neighboring vertices, a projection of which on the tooth axis is topmost in a direction of the traversing the plurality of vertices.

* * * * *